US010233425B2

(12) United States Patent
Powell, Jr.

(10) Patent No.: US 10,233,425 B2
(45) Date of Patent: Mar. 19, 2019

(54) CD137 ENRICHMENT FOR EFFICIENT TUMOR INFILTRATING LYMPHOCYTE SELECTION

(71) Applicant: The Trustees of the University of Pennsylvania, Philadelphia, PA (US)

(72) Inventor: Daniel J. Powell, Jr., Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 245 days.

(21) Appl. No.: 14/917,214

(22) PCT Filed: Sep. 16, 2014

(86) PCT No.: PCT/US2014/055866
§ 371 (c)(1),
(2) Date: Mar. 7, 2016

(87) PCT Pub. No.: WO2015/039100
PCT Pub. Date: Mar. 19, 2015

(65) Prior Publication Data
US 2016/0215262 A1    Jul. 28, 2016

Related U.S. Application Data

(60) Provisional application No. 61/878,445, filed on Sep. 16, 2013.

(51) Int. Cl.
*C12N 5/0783* (2010.01)
*A61K 35/17* (2015.01)

(52) U.S. Cl.
CPC ............ *C12N 5/0638* (2013.01); *A61K 35/17* (2013.01); *C12N 5/0636* (2013.01); *C12N 5/0646* (2013.01)

(58) Field of Classification Search
CPC .................................................. C12N 5/0638
See application file for complete search history.

(56) References Cited

PUBLICATIONS

Chacon et al., "Co-stimulation through 4-1BB/CD137 improves the expansion and function of CD8+ melanoma tumor-infiltrating lymphocytes for adoptive T-cell therapy," PLOS One 8(4):1-14, published on Apr. 1, 2013, manuscript submitted Nov. 6, 2012.*
PCT International Search Report and Written Opinion for PCT International Application No. PCT/US2014/055866 dated Dec. 22, 2014.
Aoki, et al., "Use of adoptive transfer of tumor-infiltrating lymphocytes alone or in combination with cisplatin-containing chemotherapy in patients with epithelial ovarian cancer", Cancer Res. 51(7), Apr. 1, 1991, 1934-1939.
Ascierto, et al., "Clinical experiences with anti-CD137 and anti-PD1 therapeutic antibodies", Semin Oncol. 37(5), Oct. 2010, 508-516.

(Continued)

*Primary Examiner* — Rosanne Kosson
(74) *Attorney, Agent, or Firm* — Saul Ewing Arnstein & Lehr LLP; Kathryn Doyle

(57) ABSTRACT

The invention includes compositions and methods to rapidly isolate and culture cells that are potent for use in adoptive immunotherapy. In one embodiment, the isolated cells of the invention are tumor infiltrating lymphocytes (TIL) that express CD137 (also known as 4-1BB and TNFSFR9).

13 Claims, 8 Drawing Sheets

(56) References Cited

PUBLICATIONS

Besser, et al., "Adoptive transfer of tumor-infiltrating lymphocytes in patients with metastatic melanoma: intent-to-treat analysis and efficacy after failure to prior immunotherapies", Clin Cancer Res. 19(17), Sep. 1, 2013, 4792-4800.

Besser, et al., "Clinical responses in a phase II study using adoptive transfer of short-term cultured tumor infiltration lymphocytes in metastatic melanoma patient", Clin Cancer Res. 16(9), May 1, 2010, 2646-2655.

Brahmer, et al., "Safety and activity of anti-PD-L1 antibody in patients with advanced cancer", N Engl J Med. 366(26), Jun. 28, 2012, 2455-2465.

Chacon, et al., "Co-stimulation through 4-1BB/CD137 improves the expansion and function of CD8(+) melanoma tumor-infiltrating lymphocytes for adoptive T-cell therapy", PLoS One. 8(4), Apr. 1, 2013, 1-14.

Dudley, et al., "Cancer regression and autoimmunity in patients after clonal repopulation with antitumor lymphocytes", Science. 298(5594), Oct. 25, 2002, 850-854.

Dudley, et al., "Generation of tumor-infiltrating lymphocyte cultures for use in adoptive transfer therapy for melanoma patients", J Immunother. Jul.-Aug. 2003;26(4), Jul.-Aug. 2003, 332-342.

Erdag et al., "Immunotype and immunohistologic characteristics of tumor-infiltrating immune cells are associated with clinical outcome in metastatic melanoma", Cancer Res. 72(5), Mar. 1, 2012, 1070-1080.

Freedman, et al., "Large-scale expansion in interleukin-2 of tumor-infiltrating lymphocytes from patients with ovarian carcinoma for adoptive immunotherapy", J Immunol Methods. 167(1-2), Jan. 3, 1994, 145-160.

Fujita, et al., "Prolonged disease-free period in patients with advanced epithelial ovarian cancer after adoptive transfer of tumor-infiltrating lymphocytes", Clin Cancer Res. 1(5), May 1995, 501-507.

Galon, et al., "Type, density, and location of immune cells within human colorectal tumors predict clinical outcome", Science. 313(5795), Sep. 29, 2006, 1960-1964.

Gattinoni, et al., "Adoptive immunotherapy for cancer: building on success", Nat Rev Immunol. 6(5), May 2006, 383-393.

Gattinoni, et al., "Removal of homeostatic cytokine sinks by lymphodepletion enhances the efficacy of adoptively transferred tumor-specific CD8+ T cells", J Exp Med. 202(7), Oct. 3, 2005, 907-912.

Goff, et al., "Tumor infiltrating lymphocyte therapy for metastatic melanoma: analysis of tumors resected for TIL", J Immunother. 33(8), Oct. 2010, 840-847.

Hernandez-Chacon, et al., "Costimulation through the CD137/4-1BB pathway protects human melanoma tumor-infiltrating lymphocytes from activation-induced cell death and enhances antitumor effector function", J Immunother. 34(3), Apr. 2011, 236-250.

Hwu, "Targeted therapy for metastatic melanoma: From bench to bedside", HemOnc Today. 10, 2010, 5-8.

Inozume, et al., "Selection of CD8+PD-1+ lymphocytes in fresh human melanomas enriches for tumor-reactive T cells", J Immunother. 33(9), Nov.-Dec. 2010, 956-964.

Ioannides, et al., "Cytotoxic T cell clones isolated from ovarian tumor-infiltrating lymphocytes recognize multiple antigenic epitopes on autologous tumor cells", J Immunol. 146(5), Mar. 1, 1991, 1700-1707.

Liu, et al., "IL-15 mimics T cell receptor crosslinking in the induction of cellular proliferation, gene expression, and cytotoxicity in CD8+ memory T cells", Proc Natl Acad Sci U S A. 99(9), Apr. 30, 2002, 6192-6197.

Milne, et al., "Systematic analysis of immune infiltrates in high-grade serous ovarian cancer reveals CD20, FoxP3 and TIA-1 as positive prognostic factors", PLoS One. 4(7), Jul. 29, 2009, e6412.

Prieto, et al., "Enrichment of CD8+ cells from melanoma tumor-infiltrating lymphocyte cultures reveals tumor reactivity for use in adoptive cell therapy", J Immunother. 33(5), Jun. 2010, 547-556.

Radvanyi, et al., "Specific lymphocyte subsets predict response to adoptive cell therapy using expanded autologous tumor-infiltrating lymphocytes in metastatic melanoma patients", Clin Cancer Res. 18(24), Dec. 15, 2012, 6758-6770.

Romero, et al., "Ex vivo staining of metastatic lymph nodes by class I major histocompatibility complex tetramers reveals high numbers of antigen-experienced tumor-specific cytolytic T lymphocytes", J Exp Med. 188(9), Nov. 2, 1998, 1641-1650.

Rosenberg, et al., "Durable complete responses in heavily pretreated patients with metastatic melanoma using T-cell transfer immunotherapy", Clin Cancer Res. 17(13), Jul. 1, 2011, 4550-4557.

Sato, et al., "Intraepithelial CD8+ tumor-infiltrating lymphocytes and a high CD8+/regulatory T cell ratio are associated with favorable prognosis in ovarian cancer", Proc Natl Acad Sci U S A. 102(51), Dec. 20, 2005, 18538-18543.

Schluns, et al., "Cytokine control of memory T-cell development and survival", Nat Rev Immunol. 3(4), Apr. 2003, 269-279.

Sznol, et al., "Phase I study of BMS-663513, a fully human anti-CD137 agonist monoclonal antibody, in patients (pts) with advanced cancer (CA)", Journal of Clinical Oncology, 2008 ASCO Annual Meeting Proceedings (Post-Meeting Edition). vol. 26, No. 15S (May 20 Supplement), 2008, 3007 (Abstract Only).

Topalian, et al., "Safety, activity, and immune correlates of anti-PD-1 antibody in cancer", N Engl J Med. 366(26), Jun. 28, 2012, 2443-2454.

Wolfl, et al., "Activation-induced expression of CD137 permits detection, isolation, and expansion of the full repertoire of CD8+ T cells responding to antigen without requiring knowledge of epitope specificities", Blood. 110(1), Jul. 1, 2007, 201-210.

Ye, et al., "Engineered artificial antigen presenting cells facilitate direct and efficient expansion of tumor infiltrating lymphocytes", J Transl Med. 9, Aug. 9, 2011, 131.

Zandvliet, et al., "Simultaneous isolation of CD8(+) and CD4(+) T cells specific for multiple viruses for broad antiviral immune reconstitution after allogeneic stem cell transplantation", J Immunother. 34(3), Apr. 2011, 307-319.

Zhang, et al., "Intratumoral T cells, recurrence, and survival in epithelial ovarian cancer", N Engl J Med. 348(3), Jan. 16, 2003, 203-213.

* cited by examiner

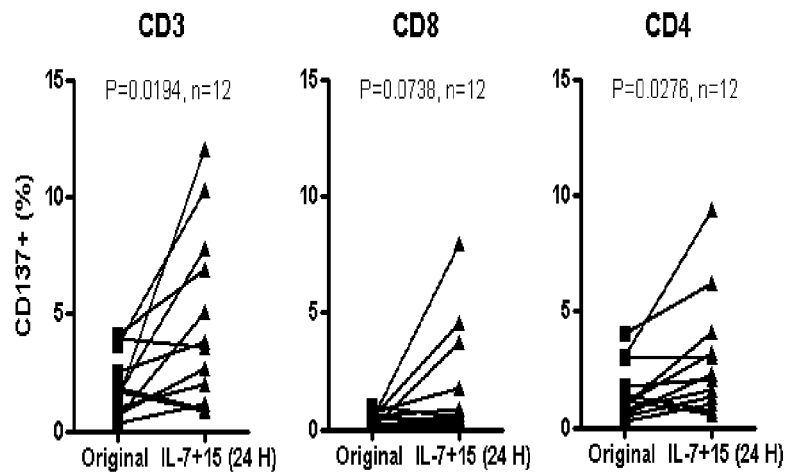
Figure 2D
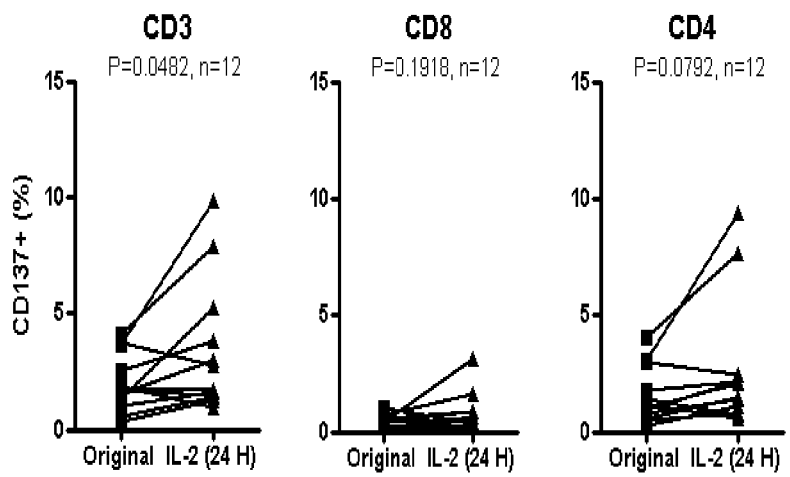
Figure 2E
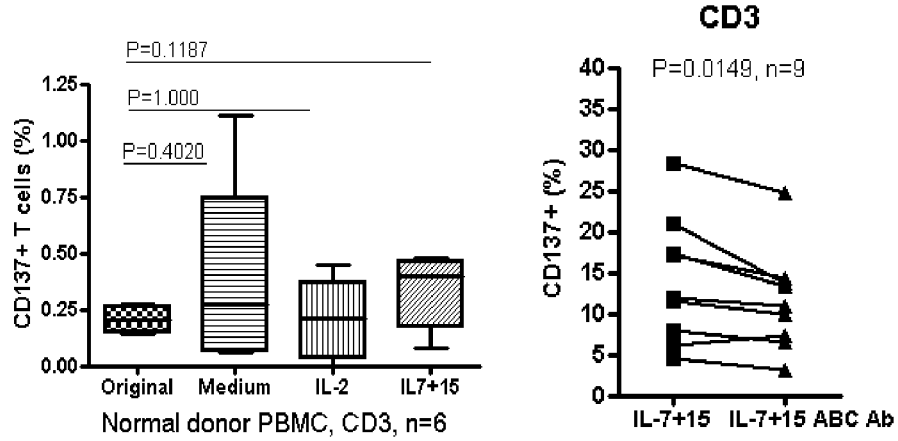
Figure 2F
Figure 2G

CD137 ENRICHMENT FOR EFFICIENT TUMOR INFILTRATING LYMPHOCYTE SELECTION

CROSS-REFERENCE TO RELATED APPLICATIONS

The present application is a 35 U.S.C. § 371 national phase application from, and claims priority to, International Application No. PCT/US2014/055866 filed Sep. 16, 2014, and published under PCT Article 21(2) in English, which claims priority under 35 U.S.C. § 119(e) to U.S. Provisional Application No. 61/878,445, filed Sep. 16, 2013, the entire disclosure of which is incorporated by reference herein as if set forth herein in its entirety.

STATEMENT REGARDING FEDERALLY SPONSORED RESEARCH OR DEVELOPMENT

This invention was made with government support under grant number RO1-CA168900 awarded by the National Institutes of Health. The government has certain rights in the invention.

BACKGROUND OF THE INVENTION

T-cells with anti-tumor potential have shown importance in the application of immunotherapy to treat cancers. The clinical efficacy of non-specific immunomodulatory agents, including immunostimulatory cytokines and antibodies that block negative immunoregulatory molecules or engage agonistic receptors on T-cells, supports the notion that cancer immunity can be manipulated to mediate tumor regression. However, numerous clinical trials administering immunomodulatory agents continue to be halted due to deleterious side effects or worsening of disease. Additionally, the association between intratumoral T-cell accumulation and improved survival in cancer (Zhang et al., 2003, N Engl J Med, 348: 203-13; Galon et al., 2006, Science, 313: 1960-4; Erdag et al., 2012, Cancer Res, 72: 1070-80) predicts a role for tumor-specific T-cell activity in tumor control.

Following antigen-induced stimulation, human T-cells undergo dynamic functional and phenotypic changes, including upregulated surface expression of multiple activation-associated molecules, including CD25, CD69, CD38 and others. The upregulation of surface molecules provides the opportunity to identify and isolate antigen-specific T-cells through antibody binding of the upregulated determinant and subsequent enrichment by magnetic separation or fluorescence-activated cell sorting (FACS).

Immune targeting of tumor antigens that are overexpressed by cancer cells in numerous cancer types with limited expression in normal tissues holds significant promise for widespread clinical application. However, the identification of new immunogenic epitopes from pre-defined antigens or specific tumor types remains a challenge.

To isolate and study naturally-occurring tumor-reactive T-cells, tumors represent a more promising reservoir than blood. An increased relative frequency of defined tumor antigen-specific T-cells reside in tumors (Romero et al., 1998, J Exp Med, 188:1641-50). Unlike in blood, naturally-occurring tumor-reactive T-cells may express activation-associated molecules as a product of direct interaction with tumor cells (Milne et al., 2009, PLoS ONE, 4:e6412).

However, isolation and expansion of tumor-reactive T-cells has been poor at best. Tumor-reactive T cells require activation to express activation-associated molecules on their surfaces. Limited activation of these cells has been achieved with ex vivo stimulation using viral antigens (Wolfl et al., 2007, Blood, 110: 201-10). Stimulation with cytomegalovirus, Epstein-Barr virus, influenza or human adenovirus antigens created reactive T-cells, but the T cells were limited to only virus specific antigens (Zandvliet et al., 2011, J Immunother, 34: 307-19).

Therefore, there is an urgent need in the art for compositions and methods for identifying tumor antigen-specific T-cells and expansion of such cells for the treatment of cancer.

SUMMARY OF THE INVENTION

The invention includes compositions and methods to rapidly isolate and culture cells that are potent for use in adoptive immunotherapy.

In one aspect, the invention includes a method of culturing tumor-reactive T cells, the method comprising isolating and culturing a population of CD137+ cells from a sample of solid tumor tissue, wherein the population of CD137+ cells comprises the tumor-reactive T cells.

In another aspect, the invention includes tumor-reactive T cell isolated according to the method described herein.

In yet another aspect, the invention includes a method of treating a tumor in a patient, the method comprising administering to a patient in need thereof an effective amount of a population of CD137+ cells, wherein the cells are isolated and cultured from a sample of solid tumor tissue.

In still yet another aspect, the invention includes using a population of CD137+ cells in the manufacture of a medicament for the treatment of a solid tumor. In another aspect, the invention includes a method of culturing tumor-reactive T cells, the method comprising isolating and culturing CD137+ cells from a sample of solid tumor tissue in a closed-chamber, wherein the population of CD137+ cells comprises the tumor-reactive T cells.

In various embodiments of the above aspects or any other aspect of the invention delineated herein, the invention includes the population of CD137+ cells comprises one or more of tumor-infiltrating lymphocytes (TIL), cytotoxic T lymphocytes (CTL), natural killer (NK) cells, and lymphokine-activated killer (LAK) cells. In another embodiment, the population of CD137+ cells comprises PD-1+ cells.

In one embodiment, the solid tumor tissue comprises cancer cells. In another embodiment, the solid tumor tissue comprises tumor antigens that have been exposed to the tumor-reactive T cells.

One embodiment of the method further comprises enzymatically digesting the solid tumor tissue prior to isolating and culturing the population of CD137+ cells. Another embodiment further comprises culturing the population of CD137+ cells in the presence of at least one of IL-2, IL-7 and IL-15. Yet another embodiment further comprises administering the population of CD137+ cells to a subject in need thereof. The method can further comprise culturing the population of CD137+ cells for about 7 days prior to administering to the subject. The method can also further comprise expanding the population of CD137+ cells prior to administering to the subject.

Another embodiment of the method further comprises culturing the population of CD137+ cells in a presence of an immune cell stimulating ligand. The immune cell stimulating ligand may be at least one selected from the group consisting of an anti-CD3 antibody and an anti-CD28 antibody.

In one embodiment, the method further comprises co-culturing the population of CD137+ cells with a HLA-matched tumor cell line. In such an embodiment, the population of CD137+ cells may produce IFN-γ after co-culturing with the HLA-matched tumor cell line. In another embodiment, the population of CD137+ cells are autologous to the patient.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising (FIG. 1A) CD137 staining on the CD3+ T cell population compared to the isotype control on TILs, TALs and PBMC. Plots representative of staining performed on n=12 (TILs), n=13 (TALs) or n=6 (PBMC) samples. (FIG. 1B) CD137 expression for all patient TILs, TALs and PBMC assessed. (FIG. 1C) CD137 expression on viable, CD3+, CD8+ and CD4+(CD3+CD8−) T cell subpopulation of TILs and TALs. P values were determined by Student t-test.

FIG. 2, comprising FIGS. 2A-2G, depicts the results of experiments demonstrating that CD137 expression on TILs and TALs is upregulated by common gamma chain cytokines IL-7 and IL-15 and inhibited by anti-HLA class I antibody. (FIG. 2A) A single-cell suspension of fresh enzymatically-digested solid tumor or ascites from a representative ovarian cancer patient was stained with antibodies for EpCAM (tumor cells), CD45 (leukocytes) and 7-AAD and viable cells analyzed by flow cytometry. Representative plots showing gating strategy for CD45+ leukocytes are shown. (FIG. 2B) CD137 expression on CD45-gated CD3+, CD8+ and CD4+(CD3+ CD8−) TILs before and after overnight culturing in complete medium containing 50 ng/mL each of IL-7 and IL-15. (FIG. 2C) CD137 expression on CD3+, CD4+ and CD8+ TILs before and after overnight culture in complete media containing 50 IU/mL IL-2. (FIG. 2D) CD137 expression on CD3+, CD4+ and CD8+ TALs from ascites before and after overnight culturing in 50 ng/mL each of IL-7 and IL-15. (FIG. 2E) CD137 expression on CD3+, CD4+ and CD8+ TALs before and after overnight culturing in 50 IU/mL IL-2. (FIG. 2F) CD137 expression on CD3+ T cells in patient PBMC cultured in complete media alone or with IL-2 or IL-7 plus IL-15. (FIG. 2G) CD137 expression on CD3+ T cells in ovarian cancer patient TILs after overnight incubation with anti-HLA-ABC antibody in vitro. P values were determined by Student t-test.

FIG. 3, comprising (FIG. 3A) Purity of enriched CD137$^{pos}$ T cells from ovarian cancer patient TILs and TALs cultured overnight in 50 ng/mL each of IL-7 and IL-15 after CD137 magnetic cell separation (MACS). The CD137-enriched or eluted fraction of TILs (FIG. 3B) or TALs (FIG. 3C) were then cultured for 8-10 days in CM and 50 IU/mL IL-2. Representative data from donor 1745 shows IFN-g production (pg/ml±SEM) from CD137$^{pos}$ or CD137$^{neg}$ TIL or TAL cultures from an HLA-A2+ donor after stimulation with autologous tumor, HLA-matched (OVCAR5) or mismatched (SKOV3) ovarian cancer cell lines and HLA-A2+ 624 or HLA-A2− 938 melanoma cell lines, as measured by human IFN-g ELISA. Results are representative of six independent assays.

FIG. 4, comprising (FIG. 4A) Melanoma TIL cell lines (TILs #1, 2, 3 and 4) were analyzed for CD137 expression and MART-1 tetramer positive staining on viable CD3+ cells by flow cytometry before and after overnight co-culture with HLA-matched (624 mel) or mismatched (938 mel) tumor cell lines in vitro. (FIG. 4B) TILs from overnight co-cultures were enriched for CD137$^{pos}$ T cells by magnetic cell separation, further cultured for 7 days then stimulated overnight in triplicate with MART-1:26-35(27L) or irrelevant HER2 peptide-pulsed T2 cells, HLA-matched melanoma lines 526 mel or 624 mel or HLA-mismatched melanoma line 938 mel, and supernatants measured for IFN-g concentration. Histograms show CD137 expression on representative TIL#2 following cell enrichment. Mean IFN-g concentration from triplicate culture is shown in pg/mL±SEM. (FIG. 4C) NGS mice co-inoculated with firefly luciferase-transfected 624 melanoma cells and the indicated TIL population were monitored via bioluminescence signal detection or caliper measurement. Image of luciferase-transfected 624 tumor luminescence in mice receiving unmanipulated, CD137$^{pos}$ or CD137$^{neg}$ TILs in a subcutaneous melanoma model. (FIG. 4D) Caliper-based measurement of subcutaneous 624 tumor growth in vivo. Tumor volume is shown. (FIG. 4E) Macroscopic visualization and sizing of tumors from the various treatment groups resected after 51 days after inoculation.

FIG. 5, comprising (FIG. 5A) Representative TILs from ovarian cancer patient digested tumor (Ov1938) or a melanoma TIL line (MEL1931) were stained with 7-AAD for viability, anti-CD137, anti-CD3 and anti-PD-1 or isotype control antibodies either fresh or after overnight incubation with 50 ng/mL of IL-7 and IL-15 each. For MEL1931 TILs, cells were co-cultured overnight in the presence of HLA-matched 624 melanoma cells. Stimulated MEL1931 TIL subsets were then sorted by FACS and rested in low IL-2 (100 IU/ml) conditions for 9 days prior to overnight co-culture with 624 mel or 938 mel tumor cells or peptide pulsed T2 cells. (FIG. 5B) IFN-g production by sorted CD137$^+$PD-1$^+$ and CD137$^+$PD-1$^-$ subsets but not CD137$^-$PD-1$^+$ TIL following stimulation with 624 mel. (FIG. 5C) MART-1 peptide-specific reactivity was limited to CD137$^+$PD-1$^+$ and CD137$^+$PD-1$^-$ subsets. TILs subsets were co-cultured overnight with T2 cells loaded with 1 uM MART-1 or p53 peptides. Mean IFN-g concentration from triplicate cultures is shown in pg/mL±SEM.

FIG. 6, comprising (FIG. 6A) Ovarian cancer TALs from donor 1555 were co-cultured with the HLA-matched tumor cell line OVCAR5, the HLA-matched melanoma line 624 mel, anti-CD3 and anti-CD28-coated microbeads or with CM alone. Co-cultures were established in the presence of anti-HLA-ABC antibody, an isotype control or nothing. IFN-g production was assessed by ELISA in co-culture supernatant after overnight culture. (FIG. 6B)

Figure 1A:
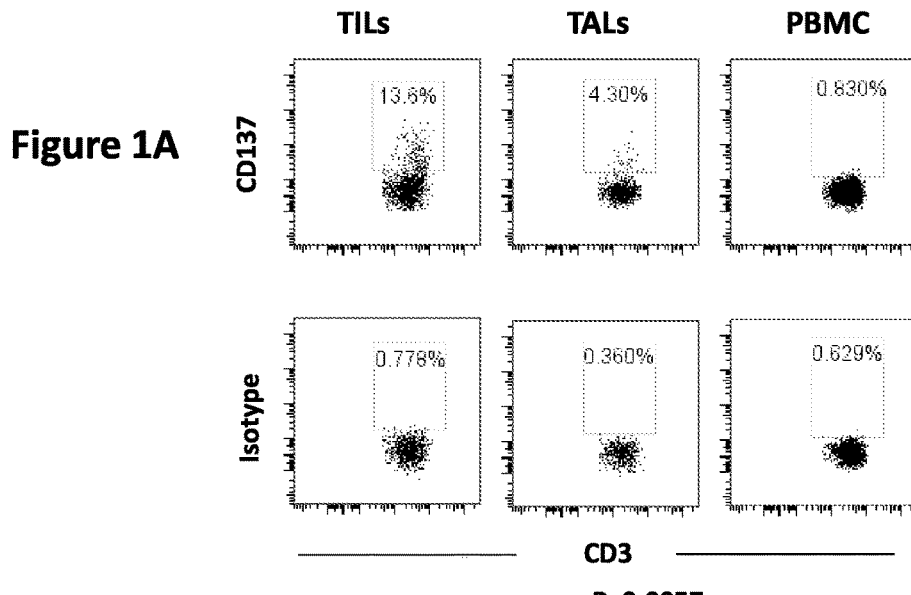
FIGS. 1A-1C, depicts the results of experiments demonstrating that naturally occurring CD137+ T cells exist in human ovarian cancer. CD137 expression on TILs, TALs and PBMC from patient samples. All samples were stained with anti-CD3, CD8 and CD137 antibodies, gated on viable cells (7-AAD-) and examined by flow cytometry.

CD137 expression by CD8+ T cells in TAL1555 following overnight co-culture with HLA-matched OVCAR5 ovarian or 624 melanoma cancer cells with or without anti-HLA-ABC antibodies by flow cytometric analysis.

FIG. 7, comprising FIGS. 7A-7D, depicts the results of experiments demonstrating that CD137-enriched ovarian cancer TILs slow tumor growth in vivo. Ovarian cancer line TAL (1555) were expanded to large numbers in IL-2 and co-cultured overnight with OVCAR5 cancer cells in 50 ng/mL each of IL-7 and IL-15. (FIG. 7A) TILs from co-cultures were stained with CD137 and CD3-specific antibodies and viable TILs analyzed for phenotype by flow cytometry. (FIG. 7B) Surface expression of CD137 by tumor-exposed $CD137^{pos}$ and $CD137^{neg}$ TILs subsets following CD137 antibody-based cell separation. (FIG. 7C) $10^6$ unmanipulated, $CD137^{pos}$ or $CD137^{neg}$ TIL fractions were grown separately for 10 days in 50 IU/mL IL-2, then co-inoculated into NSG mice subcutaneous with an equal number of luciferase-transfected OVCAR5 ovarian cancer cells. Tumor volume ($mm^3$) was monitored longitudinally. (FIG. 7D) Macroscopic sizing of tumors resected 51 days post-inoculation.

DETAILED DESCRIPTION

The present invention describes the identification, validation and expansion of spontaneous tumor-reactive tumor-infiltrating lymphocytes (TILs) to better understand the immunobiology of cancer and create improved immunotherapies.

The invention is based partly on the discovery that tumor-reactive TILs found in a tissue sample, such as solid tumor tissue, express CD137 surface makers. The invention includes compositions and methods for isolating and culturing cells for use in adoptive immunotherapy. In one embodiment, the isolated cells are tumor infiltrating lymphocytes (TIL) that express CD137 (also known as 4-1BB and TNFSFR9). In another embodiment, the TILs are positive for both CD137 and PD-1.

In one aspect, the invention includes a method of identifying tumor-reactive T cells from a patient tumor sample, such as a solid tumor, based on the expression of at least CD137. In another embodiment, the tumor-reactive T cells are isolated from a patient tumor sample, such as a solid tumor, based on the expression of at least CD137 and PD-1.

In one embodiment, the tumor-reactive T cells of the invention are isolated and the cells are culture expanded to a desired quantity for administration to a patient in need thereof (e.g., an adoptive cell transfer ACT regimen).

In another embodiment, selection of the tumor-reactive TIL from a patient's tumor is based on the markers of the invention. The cells are isolated prior to re-infusion into the patient. One advantage of the invention is that the in vitro culture time is reduced to obtain the desired number of tumor-reactive T cells, thereby providing an effective anti-cancer T cell product for immunotherapy.

DEFINITIONS

Unless defined otherwise, all technical and scientific terms used herein have the same meaning as commonly understood by one of ordinary skill in the art to which the invention pertains. The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "CD137" refers to a TNFR-family member with costimulatory function. CD137 is also called 4-1BB or TNFSFR9. It was originally identified as an inducible molecule expressed on activated mouse and human CD8+ and CD4+ T-cells (Watts, 2005, Annu Rev Immunol, 23: 23-68; Vinay et al., 1998, Semin Immunol, 10: 481-9; Kwon and Weissman, 1989, Proc Natl Acad Sci USA, 86: 1963-7). CD137 signaling regulates T-cell proliferation and survival, particularly within the T-cell memory pool (Shuford et al., 1997, J Exp Med, 186: 47-55; Suhoski et al., 2007, Mol Ther, 15:981-8; Takahashi et al., 1999, J Immunol, 162: 5037-40) and can upregulate Bcl-$X_L$ anti-apoptotic protein expression (Lee et al., 2002, J Immunol, 169:4882-8) and supports CD8+ T-cell expansion (Suhoski et al., 2007, Mol Ther, 15:981-8; Ye et al., 2011, J Transl Med, 9:131).

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, such as a mammal, or cells thereof whether in vitro or in situ, amenable to the methods described herein. In certain non-limiting embodiments, the patient, subject or individual is a human.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for isolating and culturing tumor-reactive T-cells. In one embodiment, the invention provides compositions and methods to isolate and culture tumor infiltrating lymphocytes (TILs) having tumor-rejecting capability.

The invention includes compositions and methods for rapidly isolating and culturing cells for use in adoptive immunotherapy. In one embodiment, the isolated cells of the invention are tumor infiltrating lymphocytes (TILs) that express CD137 (also known as 4-1BB and TNFSFR9). In some instances, the TILs of the invention express both CD137 and PD-1.

In one aspect, the invention includes the use of CD137 as a marker for identifying and isolating naturally-occurring, tumor-reactive TILs. In one embodiment, CD137 is a marker for selective enrichment of tumor-reactive TIL populations for developing adoptive immunotherapies. In one embodiment, the method includes culturing tumor-reactive T cells comprising isolating and culturing a population of CD137+ cells from a sample of solid tumor tissue. In such an embodiment, the population of CD137+ cells may include the tumor-reactive T cells.

In another aspect, the invention includes enriching and expanding CD137 positive cells for use in a cellular therapy for adoptive transfer. In one embodiment, CD137 positive cells are selectively isolated from a tumor specimen. In another embodiment, CD137 positive cells are selectively isolated from a population of TILs co-cultured with HLA-matched tumor cell lines. In yet another embodiment, the CD137 positive cells produce IFN-γ after exposure to autologous tumor cells.

In yet another aspect, the isolated CD137 cells of the invention are cultured in the presence of IL-2. In some instances, the CD137 cells of the invention are cultured for about 1 week prior or about 7 days prior to administering the cells to a subject in need thereof. In this manner, a shortened culture duration as compared to other prior art methods enriches and expands the tumor-reactive fractions, resulting in improved production of immunotherapies.

In still another aspect, the invention includes a method of treating a tumor in a patient comprising administering to a patient in need thereof an effective amount of a population of CD137+ cells. In this embodiment, the CD137+ cells may be isolated and cultured from a sample of solid tumor tissue.

Sources of T Cells

Adoptive immunotherapy has often failed because the transferred immune cells were inactive in vivo. The invention described herein provides a method of producing immune cells that are highly active in vivo. The immune cells may be tumor-infiltrating lymphocytes (TIL), cytotoxic T lymphocytes (CTL), natural killer (NK) cells, or lymphokine-activated killer (LAK) cells, for example. The methods described herein may be used to treat a number of diseases including cancer, infectious diseases, and immunodeficiencies. In one embodiment, the CD137+ cells are autologous to the patient. In such circumstances, the cells transferred into the patient are the patient's own cells to prevent rejection or adverse immune reactions to the administered cells.

Various immune cells may be used in adoptive immunotherapy. Immune cells, such as lymphocytes, may be used. In some embodiments, the immune cells comprise adaptive immune cells. In some embodiments, the immune cells comprise innate immune cells (such as natural killer cells or macrophages or neutrophils).

Lymphocytes are well known in the art and include T-lymphocytes, which carry T-cell receptors, B-lymphocytes, which produce antibodies, TIL, CTL, NK cells, and LAK cells. Any one lymphocyte produces one type of TCR or antibody. Each TCR or antibody has specificity for one particular epitope, or antigen binding site, on its cognate antigen. Specific TCRs or antibodies are encoded by genes that are formed from the rearrangement of DNA in a lymphocyte stem cell that encodes the constant ("C"), joining ("J"), variable ("V") regions, and possibly diversity ("D") regions of the TCR or antibody. Mammals typically possess one-hundred thousand to one-hundred million lymphocytes of different specificities. Upon stimulation of lymphocytes by an antigen, those lymphocytes specific for the antigen undergo clonal amplification.

T lymphocytes are formed in the bone marrow, migrate to and mature in the thymus and then enter the peripheral blood and lymphatic circulation. T lymphocytes are subdivided into three distinct types of cells: helper T cells, suppressor T cells, and cytotoxic T cells. T lymphocytes, unlike B lymphocytes, do not produce antibody molecules, but express a heterodimeric cell surface receptor that recognizes peptide fragments of antigenic proteins that are attached to proteins of the major histocompatibility complex (MHC) and expressed on the surfaces of target cells. T lymphocytes include tumor-infiltrating lymphocytes.

Cytotoxic T lymphocytes (CTL) are well known in the art and are typically of the CD3+, CD8+, CD4− phenotype. They typically lyse cells that display fragments of foreign antigens associated with class I MHC molecules on their cell surfaces. CTL typically recognize normal cells expressing antigens after infection by viruses or other pathogens; and tumor cells that have undergone transformation and are expressing mutated proteins or are over-expressing normal proteins.

Natural Killer (NK) cells are well known in the art. NK cells are a subset of lymphocytes active in the immune system and representing an average 15% of mononuclear cells in human peripheral blood. Among the surface markers used to identify human NK cells is a receptor binding with low affinity to the Fc fragment of IgG antibodies, such as Fc-γ receptor III or CD16 antigen. NK cells have been demonstrated to play an important role in vivo in the defense against tumors, tumor metastases, virus infection, and to regulate normal and malignant hematopoiesis.

Lymphokine-activated killer (LAK) cells are well known in the art and are a cytotoxic population of cells which are capable of lysing autologous tumor cells and NK-cell resistant tumor cell lines. Precursors of LAK cells belong to the subpopulation of "null" lymphocytes that bear neither T nor B cell surface markers. In the human these precursor cells are widely found in peripheral blood, lymph nodes, bone marrow and the thoracic duct.

In another aspect, a population of CD137+ cells are isolated from a liquid tumor tissue, such as peripheral blood, bone marrow, or ascites Immune cells such as lymphocytes (e.g., TIL, CTL, NK cells, and LAK cells) may be isolated using a variety of methods known in the art. For example, one method of isolating CTL is described in U.S. Pat. No. 6,805,861, wherein allo-restricted CTL were generated by in vitro stimulation of native splenocytes with an appropriate antigen. Alternatively, one may obtain CTL using a method described in U.S. Pat. No. 6,531,451, wherein a blood sample containing T-cell precursors is taken from a mammal, and PBLs are purified from such blood sample and are incubated with stimulator cells which express antigenic peptides complexed with the appropriate MHC molecule. Isolation of NK cells is described in U.S. Pat. No. 7,435,596. Specifically, human primary NK cells may be expanded in the presence of a myeloid cell line that has been genetically modified to express membrane bound IL-15 and 4-1BB ligand. LAK cells may be generated, for example, by treating a patient's mononuclear lymphocytes with interleukin-2, as described in U.S. Pat. Nos. 5,002,879, 4,849,329 and 4,690,915. Mononuclear lymphocytes may be collected, for example, by repeated lymphocytophereses using a continuous flow cell separator as described in U.S. Pat. No. 4,690,915. In some embodiments, the immune cells such as lymphocytes (e.g., TIL, CTL, NK cells, or LAK cells) are isolated using an affinity purification step such as FACS, MACS, or batch purification using an antibody against an appropriate surface antigen. In some instances, a clonal population of immune cells such as lymphocytes (e.g., TIL, CTL, NK cells, or LAK cells) is obtained. In other instances, the population is not clonal.

In one embodiment, tumor-reactive T cells are isolated from solid tumor tissue comprising a population of CD137+ cells. In most instances, the tumor tissue comprises a heterogenous mixture of cells and cell types, including cancerous cells and the population of CD137+ cells comprising the tumor-reactive T cells. The tumor tissue may also include tumor antigens. In a preferred embodiment, the tumor antigens have been exposed to and stimulated the tumor-reactive T cells. The tumor tissue is removed from the patient prior to selectively isolating the CD137+ cells. The CD137+ cells can further be enriched for the tumor-reactive T cells by culturing the CD137+ cells in the presence of IL-2. The CD137+ cells can further be enriched for the tumor-reactive T cells by further isolating PD-1+ cells.

Another embodiment includes obtaining T cells from tumor tissue. The tumor tissue may include cancerous cells. The T cells may be isolated from the bulk of the tumor tissue prior to culturing or expansion, such as by flow cytometry, negative or positive selection, or other methods.

The invention also includes a method of obtaining an expanded number of TILs from a subject for adoptive cell immunotherapy comprising obtaining a tumor tissue sample from the subject and isolating CD137+ cells from the tumor tissue. That is, the invention is based partly on the discovery that highly tumor-reactive TILs found in a bulk population of cells obtained from a patient tumor sample reliably exhibit high expression CD137.

The present invention encompasses methods and kits for the isolation and expansion of a population of tumor-reactive T cells having a CD137+ phenotype. By way of example, a cell that is "CD137+" or that "expresses CD137" is contrasted herein to a cell that is CD137− or does not express a detectable level of CD137. A cell that is "CD137dim," as used herein has a lower detectable level of CD137 expression than a CD137+ cell or a "CD137bright" cell. In one embodiment, the tumor-reactive T cells are positive for both CD137 and PD-1. By way of example, a cell that is "CD137+PD-1+" or that "expresses CD137 and PD-1" is contrasted herein to a cell that is CD137-PD-1+, CD137+PD-1− or does not express a detectable level of either CD137 or PD-1.

The present invention encompasses a method for isolating CD137+ cells using a straightforward direct antibody-based purification system for isolating such cells. However, any cellular isolation methodology can be used to isolate the cells of the invention from a biological sample. For example, an antibody that binds to CD137 can be bound to a physical support, such as a magnetic bead, a dynal bead, a microbead, a column, an adsorption column, and an adsorption membrane. Conjugating an antibody to a physical support is well known in the art. Alternatively, an antibody conjugated to a physical support, such as a magnetic bead, can be purchased from a variety of sources, such as Milteny Biotec (Auburn, Calif.).

A variety of antibodies are useful in the present invention. As will be understood by one skilled in the art, any antibody that can recognize and bind to a CD antigen of interest, such as CD137 is useful in the present invention. Methods of making and using such antibodies are well known in the art. For example, polyclonal antibodies useful in the present invention are generated by immunizing rabbits according to standard immunological techniques well-known in the art.

However, the invention should not be construed as being limited solely to methods and compositions including these antibodies or to these portions of the protein antigens. Rather, the invention should be construed to include other antibodies, as that term is defined elsewhere herein, to other desired surface marker proteins, or portions thereof. Further, the present invention should be construed to encompass antibodies, inter alia, bind to the desired proteins and they are able to bind the protein present on Western blots, in solution in enzyme linked immunoassays, in FACS assays, in magnetic-actived cell sorting (MACS) assays, and in immunofluorescence microscopy.

Various techniques may be employed to separate a CD137 cell bound to an antibody, such as an anti-CD137 antibody, from cells that do not have an antibody bound cell surface marker by removing antibody-bound cells from the cell mixture.

Procedures for separation may include magnetic separation, using antibody-coated magnetic beads or dynal beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique. Techniques providing accurate separation include fluorescence activated cell sorters, which can have varying degrees of sophistication, e.g., a plurality of color channels, low angle and obtuse light scattering detecting channels, impedance channels, etc., as well as magnetic activated cell sorters.

Conveniently, the antibodies may be conjugated with markers, such as magnetic beads, which allow for direct separation, biotin, which can be removed with avidin or streptavidin bound to a support, fluorochromes, such as FITC, which can be used with a fluorescence activated cell sorter, or the like, to allow for ease of separation of the particular cell type. Any technique may be employed which is not unduly detrimental to the viability of the remaining cells. Other techniques include, but are not limited to, dense particles for density centrifugation, an adsorption column, an adsorption membrane, and the like.

The present invention further comprises a method of multiplying, expanding or otherwise culturing the isolated CD137+ cells using the methods disclosed herein. For example, multiplying a CD137+ cell isolated by the methods of the present invention can by multiplied by about 2-fold to about 1000 fold using the methods disclosed herein. Following isolation, a CD137+ cell is incubated in cell medium in a culture apparatus for a period of time before passing the cells to another culture apparatus. The culturing apparatus can be of any culture apparatus commonly used in culturing cells in vitro. A period of time can be any time suitable for the culture of cells in vitro. In one embodiment, the CD137+ cells are cultured for about 7 days to enrich or expand the tumor-reactive T cells in the culture prior to administration to a subject. In another embodiment, the CD137+ cells are cultured for about 1 day, 2 days, 3 days, 4 days, 5 days, 6 days, 7 days, 8 days, 9 days, 10 days, 11 days, 12 days, 13 days, 14 days, or longer or any amount of time therebetween.

Cell medium may be replaced during the culturing of the CD137+ cells at any time. Preferably, the cell medium is replaced every 3 to 4 days. The CD137+ cells are then harvested from the culture apparatus whereupon the CD137+ cells can be used immediately or cryopreserved to be stored for use at a later time.

In one aspect, the invention includes a method of culturing tumor-reactive T cells comprising isolating and culturing CD137+ cells from a sample of solid tumor tissue in a closed-chamber. By culturing the CD137+ cells in a closed chamber or sealed apparatus would prevent or substantially reduce the risk of contaminating the CD137+ cells during the culturing steps of the method. The closed chamber or sealed apparatus may include any appropriate culture vessel used in clinical laboratories for producing cellular therapies.

In one embodiment, the CD137+ cells can be cultured in the presence of IL-2. In one embodiment, the CD137+ cells can be cultured in the presence of an immune cell stimulating ligand, such as at least one of anti-CD3 antibody and/or anti-CD28 antibody. In one embodiment, the CD137+ cells can be cultured in the presence of anti-CD3 antibody and/or anti-CD28 antibody and in IL-2.

In another embodiment, the anti-CD3 and/or anti-CD8 antibodies are bound to beads that are cultured with the CD137+ cells. The anti-CD3/CD28 antibodies may be immobilized on the beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD137+ cell expansion and cell growth is used. In certain aspects of the present invention, a ratio of anti CD3:CD28 antibodies bound to the beads is used such that an increase in cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

In another embodiment, the CD137 positive cells are selectively isolated and co-cultured with HLA-matched tumor cell lines. Examples of HLA-matched tumor cell lines may include allogeneic cancer cell lines (Dudley et al., 2003, J Immunother, 26: 332-42), HLA-matched melanoma cell lines, autologous cancer cells, and any other cells that are HLA-matched to the CD137+ cells. In yet another embodiment, the CD137 positive cells produce IFN-γ after exposure to HLA-matched tumor cell lines, such as autologous tumor cells.

In one embodiment of the present invention, the mixture may be cultured for several hours (about 3 hours) to about 14 days or any hourly integer value in between. In another embodiment, the mixture may be cultured for 21 days. In one embodiment of the invention the CD137+ cells are cultured for about seven days.

Conditions appropriate for cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

Methods of Treating Cancer, Immunodeficiency Diseases, and Infections

The cells of the invention may be administered to a patient suffering from any impairment in immune activity (such as lymphocyte activity, natural killer cell activity, etc.). For instance, the patient may have a hypoxic tumor that is resistant to untreated immune cells. Alternatively, the patient may suffer from an infectious disease such as a viral infection, bacterial infection, fungal infection, or other eukaryotic cell infection (i.e., protozoal). Diseases with inflammatory pathogenesis typically have tissue microenvironments that are hypoxic and extracellular adenosine rich. Thus, the compositions and methods herein may be used to treat any disease that causes inflammation. The compositions and methods herein may also be used to treat any disease in which there is need to increase the potency of anti-pathogen T cells.

In one embodiment, the invention includes a method of treating a tumor in a patient comprising administering to a patient in need thereof an effective amount of a population of CD137+ cells. The CD137+ cells can be isolated from a sample of solid tumor tissue prior to the administration. In some instances, the CD137+ cells are enriched and/or expanded prior to administration.

In other embodiments, the patient may have an immunodeficiency, such as a cell type that is unusually sensitive to adenosine of an excess of adenosine. For example, ADA SCID is caused by a deficiency in adenosine deaminase and leads to a toxic buildup of adenosine that prevents T-, B-, and NK-cell cell maturation.

In certain embodiments, the patient has an inflammatory disease, such as asthma, autoimmune diseases (such as multiple sclerosis and rheumatoid arthritis), chronic inflammation, chronic prostatitis, diabetes (including diabetic ulcers) glomerulonephritis, hypersensitivities, inflammatory bowel diseases, pelvic inflammatory disease, reperfusion injury, rheumatoid arthritis, or vasculitis.

When the disease is a viral infection, it may be caused by (for instance) any one of a member of the Adenoviridae family (such as adenovirus), a member of the Coronavirus family (such as SARS), a member of the Picornaviridae family (such as coxsackievirus, hepatitis A virus, or poliovirus), a member of the Herpesviridae family (such as Epstein-Barr virus, herpes simplex, type 1, herpes simplex, type 2, human cytomegalovirus, human herpesvirus, type 8, or varicella-zoster virus), a member of the Hepadnaviridae family (such as hepatitis B virus), a member of the Flaviviridae family (such as hepatitis C virus, yellow fever virus, dengue virus, west Nile virus), a member of the Retroviridae family (such as HIV or HTLV-1), a member of the Orthomyxoviridae family (such as influenza virus), a member of the Paramyxoviridae family (such as measles virus, mumps virus, parainfluenza virus, respiratory syncytial virus), a member of the Papovaviridae family (such as papillomavirus), a member of the Rhabdoviridae family (such as rabies virus), or a member of the Togaviridae family (such as Rubella virus). In certain embodiments, the virus is a ssDNA virus, a dsDNA virus, a ssRNA virus, or a dsRNA virus. The virus may be enveloped or non-enveloped.

In some embodiments, the disease to be treated is cancer; such as any one of breast cancer; bladder cancer; lung cancer; prostate cancer; thyroid cancer; leukaemias and lymphomas such as CML (chronic myelocytic leukaemia), ALL (acute lymphoblastic leukaemia), AML (acute myelocytic leukaemia), PML (pro-myelocytic leukaemia); colon cancer; glioma; seminoma; liver cancer; pancreatic cancer; bladder cancer; renal cancer; cervical cancer; testicular cancer; head and neck cancer; ovarian cancer; neuroblastoma and melanoma.

When the disease is a bacterial infection, it may be an intracellular or extracellular infection. In certain embodiments, the bacterium is *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospria* spp., *Hemophilus ducreyi, Corynebacterium diphtheria, Bordetella pertussis, Bordetella parapertussis, Bordetella bronchiseptica, hemophilus* influenza, *Escherichia coli, Shigella* spp., *Erlichia* spp., *Rickettsia* spp.

It will be appreciated that the methods herein may be employed with any mammal such as human, cat, dog, horse, cow, sheep or pig. In some embodiments, the subject is a vertebrate. In certain embodiments, the subject is a mammal.

In certain embodiments, the cells of the invention can be used in combination with a therapeutic agent including but is not limited to an anti-tumor, an anti-cancer agent, and the like. In particular embodiments, the anti-tumor or anti-cancer agent is a nucleic acid molecule that encodes a protein that promotes apoptosis. In certain embodiments, the anti-tumor or anti-cancer agent is an alkylating drug, a folate antagonist, a purine antagonist, a pyrimidine antagonist, a spindle poison, a podophyllotoxin, an antibiotic, a nitrosurea, an inorganic ion, a biologic response modifier, an enzyme, or a hormone.

In certain embodiments, the adoptive immunotherapy is combined with a second treatment that augments the immune response. The second treatment may be, for example, an adjuvant and/or a cytokine Examples of cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor; hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-α; platelet-growth factor; transforming growth factors (TGFs) such as TGF-α and TGF-β; insulin-like growth factor-I and -II; erythropoietin (EPO); osteoinductive factors; interferons such as interferon-α, -β and -γ colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). Cytokines include proteins from natural sources or from recombinant cell culture and biologically active equivalents of the native sequence cytokines.

In some embodiments, the subject being treated is immunocompromised (or immunodeficient). In certain embodiments, the subject is infected with human immunodeficiency virus (HIV). In other embodiments, the subject is receiving immunosuppressive therapy such as, for example, chemotherapy or radiation therapy. In certain embodiments, the immunocompromised patient suffers from an inherited immunodeficiency such as SCID. In certain embodiments, the subject is infected with a virus, bacterium, or fungus. In certain embodiments, the subject has or is suffering from one or more symptoms of smallpox, yellow fever, distemper, cholera, fowl pox, scarlet fever, diphtheria, tetanus, whooping cough, influenza, rabies, mumps, measles, foot and mouth disease, or poliomyelitis.

In other embodiments, the method further comprises the step of evaluating the subject for a marker of an induced or enhanced immune response. In certain embodiments, the method comprises evaluating the level of expression of immunoglobulin, cytokines, interferon γ, interferon β, interferon α, IL-12p40, TNF-α, or IL-17 mRNA, relative to the level before oxygen administration. In some embodiments, the disclosed therapeutics are administered until a predetermined level of an immune response is achieved.

In other embodiments, the method of treatment further comprises the step of evaluating the size of the tumor, the volume of the tumor, and/or the number of tumor cells after adoptive immunotherapy. In some embodiments, the size of the tumor, the volume of the tumor, and/or the number of tumor cells are evaluated before, during, and/or after adoptive immunotherapy. In certain embodiments, adoptive immunotherapy is performed until the tumor is reduced to a preselected size, volume, or number of cells.

In one embodiment, adoptive immunotherapy is performed in an amount and for a time to reduce the size of the tumor, the volume of the tumor, and/or the number of tumor cells, compared to the size, volume, and/or number of tumor cells prior to administration of oxygen. In certain embodiments, adoptive immunotherapy reduces the size of the tumor, the volume of the tumor, and/or the number of tumor cells to less than 100%, to less than 95%, to less than 90%, to less than 80%, to less than 70%, to less than 60%, to less than 50%, to less than 30%, or to less than 10% of its size, volume, or cell number prior to therapy. In some embodiments, the adoptive immunotherapy reduces the growth of the tumor. In certain embodiments, the adoptive immunotherapy reduces the growth rate of the tumor by 10%, by 20%, by 30%, by 40%, by 50%, by 60%, by 70%, by 80%, by 90%, or by more than 90%, as compared to the growth rate of the tumor prior to adoptive immunotherapy.

In certain embodiments, the adoptive immunotherapy increases patient survival. In some aspects, the adoptive immunotherapy increases cell death of tumor or cancer cells.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

CD137 Accurately Identifies and Enriches for Naturally-Occurring Tumor-Reactive T Cells in Tumor Up-regulation of CD137 (4-1BB) on recently activated CD8+ T-cells has been used to identify rare viral or tumor antigen-specific T-cells from peripheral blood. As described here, the immunobiology of CD137 in human cancer was evaluated and the utility of a CD137-positive separation methodology for the identification and enrichment of fresh tumor-reactive tumor-infiltrating lymphocytes (TILs) or tumor-associated lymphocytes (TAL) from ascites for use in adoptive immunotherapy was assessed.

TILs from resected ovarian cancer or melanoma were measured for surface CD137 expression directly or after overnight incubation in the presence of tumor cells with homeostatic cytokines. $CD137^{pos}$ TILs were sorted and evaluated for anti-tumor activity in vitro and in vivo. Fresh ovarian TILs and TALs naturally expressed higher levels of CD137 than circulating T-cells. An HLA-dependent increase in CD137 expression was observed following incubation of fresh enzyme-digested tumor or ascites in IL-7 and IL-15 cytokines, but not IL-2. Enriched $CD137^{pos}$ TILs, but not $PD-1^{pos}$ or $PD-1^{neg}$ $CD137^{neg}$ cells, possessed autologous tumor-reactivity in vitro and in vivo. In melanoma studies, all MART-1 (melanoma antigen recognized by T cells 1) specific CD8+ TILs up-regulated CD137 expression after incubation with HLA-matched, MART-expressing cancer cells and antigen-specific effector function was restricted to the $CD137^{pos}$ subset in vitro. $CD137^{pos}$ TILs also mediated superior anti-tumor effects in vivo, compared to $CD137^{neg}$ TILs.

The data described herein reveal a role for the TNFR-family member, CD137, in the immunobiology of human cancer where it is preferentially expressed on a tumor-reactive subset of TILs, thereby rationalizing its agonistic engagement in vivo and its use in TIL selection for adoptive immunotherapy trials.

As described herein, using primary leukocytes from patients with ovarian cancer, a preferential increase in the frequency of naturally-arising T-cells with a $CD137^{pos}$ activation phenotype was observed at sites of tumor. $CD137^{pos}$ T-cells were found in both solid tumors and ascites, with higher frequencies seen in solid tumors where TILs are in direct contact with tumor cells. Few $CD137^{pos}$ T-cells were observed in the resting peripheral blood. The results described herein are consistent with the explanation that ovarian cancers act as natural sinks for enrichment of spontaneously-arising tumor antigen-specific T-cells, and support the conclusion that ovarian cancer cells are immunogenic. This is consistent with the observed improvement in survival of patients with ovarian cancers with evidence of intraepithelial T-cell accumulation (Zhang et al., 2003, N Engl J Med, 348: 203-13; Sato et al., 2005, Proc Natl Acad Sci USA, 102: 18538-43), as well as a positive association between patient survival and the presence of intraepithelial cells expressing activated effector T-cell phenotypes (CD45RO, TIA-1, granzyme B) in high-grade serous ovarian cancer (Milne et al., 2009, PLoS ONE, 4:e6412). The results described herein are consistent with the explanation that CD137 expression predicted improved prognosis in ovarian cancer.

The findings described herein implicated a novel role for CD137, an immunologic agonistic, in the biology of tumor-reactive TILs. The observation that spontaneously-arising tumor-reactive TIL subset selectively expresses CD137 in tumors helps explain, in part, the demonstrated anti-tumor effects of agonistic anti-CD137 antibodies in preclinical studies (Ascierto et al., 2010, Semin Oncol, 37: 508-16), and the observation that CD137-signaling protects human TILs from activation-induced cell death, thereby enhancing net antitumor activity in vitro (Hernandez-Chacon et al., 2011, J Immunother, 34: 236-50; Ye et al., 2011, J Transl Med, 9:131). Mouse studies show that the hypoxic tumor microenvironment upregulated CD137 expression by TILs in a hypoxia-inducible factor (HIF)-1α dependent manner (Palazon et al., 2012, Cancer Discov, 2: 608-23), in line with the data herein, and supporting the use of CD137-targeted immunotherapy in solid tumors. In an open-label, ascending, multi-dose phase I-II study, treatment of subjects with melanoma, renal cell carcinoma (RCC), or ovarian carcinoma with single-agent anti-CD137 antibody BMS663513 showed clinical activity including partial remissions and sustained stable diseases with a manageable toxicity profile (Sznol et al., 2008, J Clin Oncol, 26(15 Suppl): 3007); a phase II randomized study in previously treated melanoma patients with stage IV disease was terminated due to high incidence of grade 4 hepatitis (Hwu, 2010, HemOnc Today, 10: 5-8).

The identification and enrichment of naturally-occurring, tumor-reactive TILs for use in clinical trials has commonly relied upon prolonged microculture of a small number of independent tumor fragments in IL-2 and subsequent screening of emerging TILs for reactivity against autologous or HLA-matched allogeneic cancer cell lines (Dudley et al., 2003, J Immunother, 26: 332-42). The limited number of fragments cultured and low detection sensitivity of the method posed the risk of excluding tumor-reactive TILs and simultaneously carrying non-reactive TILs through to the final cell product.

Using cell separation to enrich for $CD137^{pos}$ cells from either enzyme-digested tumor specimens or TILs co-cultured with HLA-matched tumor cell lines, a new methodology for rapid, comprehensive isolation of tumor-reactive TILs from various tumor types that is not dependent upon ex vivo stimulation with defined antigens is described herein. Here, CD137 expression reflects specific TCR-triggered activation signals that result from encountering tumor antigens. Only CD137-enriched TILs and TALs produced IFN-γ after exposure to autologous tumor cells; CD137$^{neg}$ TILs or TALs did not, showing that the tumor-reactive TIL fraction was enriched while the non-reactive fraction was eliminated. The lack of non-specific IFN-γ production by CD137$^{pos}$ TILs against HLA-mismatched tumor lines, and the inhibition of IFN-γ secretion with anti-HLA class I antibody during specific tumor stimulation, excluded the possibility that immune recognition was mediated by an allogeneic response, or the impact of agonistic anti-CD137 antibody binding.

The observed inhibition of both IFN-γ responses and CD137 upregulation by HLA class-I antibodies described herein was consistent with the explanation of a more prominent role for CD8+ TILs in the anti-tumor response, although both CD4+ and CD8+ TILs in freshly enzyme-digested ovarian tumors expressed CD137. In other studies, the anti-tumor effects of CD137 agonists also appeared primarily dependent upon CD8+ T-cells, although other lymphocytes, such as CD4 and NK cells, have been implicated elsewhere. A role for CD8+ T-cells in CD137$^{pos}$ TIL anti-tumor activity was also described in the study of established CD8+ melanoma TIL lines with MART-1 antigen-specificity which recognized HLA-matched, MART-1-expressing melanoma cells, where CD137 was upregulated by all MART-1 peptide-specific TILs following tumor encounter. These finding also indicated that TILs upregulated CD137 upon encounter with defined tumor antigen-derived epitopes. However the observation that melanoma TILs lacking MART-specificity, but possessing known reactivity against 624 mel cells, similarly upregulated CD137 after stimulation with tumor, indicated that TILs with heterogeneous defined and unknown tumor antigen-specificity could collectively be rapidly identified and comprehensively enriched via CD137 cell separation.

In the preclinical models of adoptive TIL therapy described herein, both unmanipulated and CD137-enriched TILs and/or TALs were able to slow tumor growth in vivo, compared to CD137$^{neg}$ TILs. However, inhibition of tumor outgrowth was enhanced by the pre-selection of TILs for tumor-reactivity based upon tumor-stimulated CD137 expression Importantly, pre-selection of the tumor-reactive fraction allowed concomitant elimination of non-reactive TILs that did not contribute to the anti-tumor effect and potentially competed with reactive TIL clones for key homeostatic cytokines after infusion into the lymphopenic host (Gattinoni et al., Nat Rev Immunol, 6: 383-93; Gattinoni et al., 2005, J Exp Med, 202: 907-12). Notably, isolation of CD137$^{pos}$ TILs for therapy as described herein was conducted over a one week period; immediate CD137-enrichment followed by one week of IL-2 culture. This abbreviated method could be useful for generating TILs for use in melanoma patients where ~70% of tumors contain TILs with tumor-reactivity at detectable levels (Goff et al., 2010, J Immunother, 33:840-7; Prieto et al., 2010, J Immunother, 33: 547-56). However, CD137 isolation may further enrich this tumor-reactive fraction and shorten culture duration, thereby extending effective TIL therapy to non-melanoma cancers.

Another important finding was the elucidation that augmented CD137 expression among tumor-reactive cytotoxic CD8+ T-cells from enzyme-digested tumor was best achieved in the presence of IL-7 and IL-15, homeostatic cytokines that supported T-cell survival and memory formation (Schluns et al., 2003, Nat Rev Immunol, 3: 269-79). Increased CD137 expression among CD8+ TILs in the presence of tumor cells was MHC dependent, ruling out activation-independent effects mediated by cytokine alone (Liu et al., 2002, Proc Natl Acad Sci USA, 99: 6192-7). Although IL-2 supported the expansion of TILs from resected cancer tissue ex vivo and has been utilized extensively in generating TIL cultures (Radvanyi et al., 2012, Clin Cancer Res, 18(24): 6758-70; Besser et al., 2010, Clin Cancer Res, 16:2646-55; Fujita et al., 1995, Clin Cancer Res, 1:501-7; Aoki et al., 1991, Cancer Res, 51:1934-9; Dudley et al., 2002, Science, 298: 850-4; Rosenberg et al., 2011, Clin Cancer Res, 17: 4550-7), CD137$^{pos}$ TIL frequencies were unchanged when cultured overnight in IL-2. Although not wishing to be bound by any particular theory, the known ability of IL-2 to promote apoptosis versus the pro-survival attributes of IL-7 and IL-15 may explain this difference. The findings described herein support the use of IL-7 and IL-15 cytokines, and reconsideration of IL-2, in clinical TIL production.

It remains possible that other activation-induced markers may permit the selection of natural tumor-reactive TILs. Inozume et al. recently demonstrated the negative immuno-regulatory molecule PD-1 to be a promising biomarker for tumor-specific TIL selection in melanoma (Inozume et al., 2010, J Immunother, 33: 956-64). The efficacy of anti-PD-1 and PD-1 antibodies in melanoma supports this position (Topalian et al., 2012, N Engl J Med, 366: 2443-54; Brahmer et al., 2012, N Engl J Med, 366: 2455-65). The results confirmed PD-1 expression on melanoma as well as ovarian TILs (~20-60%) and showed that PD-1+ TILs did indeed possess anti-tumor activity. However, as described herein, that the PD-1+ population was comprised of distinct CD137$^{pos}$ and CD137$^{neg}$ subsets, and that antigen-specific tumor-reactivity was restricted to the PD-1+CD137$^{pos}$ TIL subset. Therefore, while tumor-reactive T-cells did reside within the PD-1+ population, PD-1+CD137$^{pos}$ and PD-1+CD137$^{neg}$ subsets were functionally distinct. This was corroborated by the observation that PD-1+ TILs often resided within the CD137$^{neg}$ fraction, the fraction of TILs that did not respond to stimulation with autologous or HLA-matched tumor, or peptide-pulsed APC in vitro, nor efficiently controlled tumor outgrowth in vivo. Thus, the data described herein were consistent with the explanation that while a fraction of PD-1+ TILs possessed specific anti-tumor reactivity, tumor-induced expression of CD137 on TILs better identified genuine, recently activated tumor-specific T-cells and allowed for their efficient enrichment.

The results described herein define a role for CD137 in the immmunobiology of human cancer, where it represented an agonistic biomarker for naturally-occurring, tumor antigen-reactive TILs or TALs, rationalizing further investigations of CD137 agonistic engagement in cancer. CD137 marking also allowed for the rapid, selective enrichment of rare tumor-reactive TIL populations for the development of effective adoptive immunotherapy. Development of a reliable closed-chamber method for enrichment and outgrowth of CD137-expressing lymphocytes represents the next step towards the improvement and application of adoptive TIL therapy for patients with various forms of cancer.

The materials and methods employed in these experiments are now described.

Antibodies and Flow Cytometric Immunofluorescence Analysis

Antibodies against human CD3, CD4, CD8, PD-1 and CD137 were purchased from BD Bioscience (San Jose, Calif.). CD45 and EPCAM antibodies were purchased from Biolegend (San Diego, Calif.). 7-AAD viability staining solution was purchased from BD Bioscience. HER2:369-377 peptide (KIFGSLAFL; SEQ ID NO:1) and MART-1: 26-35(27L) (ELAGIGILTV; SEQ ID NO:2) peptide containing HLA-A2010 tetramers were purchased from Beckman Coulter, Inc. (Brea, Calif.). Cells were resuspended in FACS buffer consisting of PBS with 2% FBS (Gemini Bioproducts) and blocked with 10% normal mouse Ig (Caltag Laboratories) for 10 min on ice. $10^6$ cells in 100 µl were stained with fluoro-chrome-conjugated mAbs at 4° C. for 40 min in the dark. For viability gating, cells were briefly stained with 7-AAD solution, washed twice and analyzed for nonviable cell exclusion using a FACS Canto II (BD Biosciences).

Tumor Specimens and TIL Generation

Patients were entered into an Institutional Review Board-approved protocol and signed an informed consent prior to tissue collection. For enzymatic digestion of solid tumors, specimen was diced into RPMI-1640, washed and centrifuged at 800 rpm for 5 mM at 15-22° C., resuspended in enzymatic digestion buffer (0.2 mg/ml collagenase and 30 units/ml DNase in RPMI-1640) before overnight rotation at room temperature. Cells were then washed and used fresh or cryopreserved for later use. Ascites samples were washed and enriched for the lymphocyte/tumor fraction by Ficoll-gradient separation or RBC lysis using ACK lysing buffer (Invitrogen Life Technologies). Generation of TIL cultures was performed as described (Dudley et al., 2003, J Immunother, 26: 332-42). Briefly, 2 $mm^3$ tumor fragments were cultured in complete media (CM) comprised of AIM-V medium (Invitrogen Life Technologies, Carlsbad, Calif.) supplemented with 2 mM glutamine (Mediatech, Inc. Manassas, Va.), 100 U/ml penicillin (Invitrogen Life Technologies), 100 µg/ml streptomycin (Invitrogen Life Technologies), 5% heat-inactivated human AB serum (Valley Biomedical, Inc. Winchester, Va.) and 600 IU/ml rhIL-2 (Chiron, Emeryville, Calif.). To generate TAL lines, total ascites cells were cultured at $10^6$ cells/well of 24-well plate in CM for 3-4 weeks and T-cells harvested.

Enrichment of CD137-positive cells

Fresh enzyme-digested tumors or ascites were cultured overnight in CM containing IL-7 and IL-15 (PeproTech, Rocky Hill, N.J.) at 50 ng/ml each or rhIL-2 (50 IU/ml) overnight. For allogeneic tumor cell stimulation, heterogeneous T-cells were cultured with indicated tumor cell lines at 1:1 ratio overnight in IL-7 and IL-15. For magnetic separation, $CD137^{pos}$ cells were then isolated using a CD137 MicroBead kit according to manufacturer's instruction (Miltenyi, Auburn, Calif.). For CD137/PD-1 subset analyses, tumor-exposed TILs were stained with anti-PD-1 and anti-CD137 (BD Bioscience) and sorted by FACS using the BD FACS Aria II SORP high-speed cell sorter. The purity of enriched T-cells was >90% as determined by flow cytometry. Sorted $CD137^{pos}/PD-1^{pos}$ $CD137^{pos}/PD-1^{neg}$ and $CD137^{neg}/PD-1^{pos}$ T-cells were rested in IL-2 (100 IU/ml) containing CM for ~9 days before functional assessment.

ELISA Assay for T-Cell Function

Established tumor lines or CD45-depleted tumor cells isolated from fresh autologous ascites or enzyme-digested solid tumor cells ($10^5$ cells/well) were co-cultured overnight with equal numbers of unmanipulated or enriched TILs in triplicate in 96-well U-bottom plates in 200 uL CM. For specific antigen stimulation of isolated $CD137^{pos}$ and $CD137^{neg}$ T-cells, $10^6$ T2 cells were loaded with 1 uM MART-1:26-35(27L) or p53:264-272 peptide at 37° C. for 1 hour, then washed and co-cultured overnight with T-cells. For HLA-blocking, anti-HLA-ABC antibodies (BD Pharmingen) were added at 10 ug/well at start of culture. Supernatants were harvested and analyzed for IFN-γ by ELISA, according to manufacturer's instruction (Biolegend). Mean cytokine concentration (pg/mL) ±SD of triplicate wells is shown.

In Vivo Assays

Animals were obtained from the Stem Cell and Xenograft Core of the Abramson Cancer Center, University of Pennsylvania. Six to 12-week-old NOD/SCID/γ-chain–/– (NSG) mice were bred, treated and maintained under pathogen-free conditions in-house under IACUC-approved protocols. For melanoma and ovarian studies, 6 to 12-week-old female NSG mice were inoculated s.c. with $10^6$ of the indicated T-cells mixed with an equal number of either fLuc+624 mel cells or OVCAR5 cells. Tumor dimensions were longitudinally measured with calipers, and tumor volumes calculated as $V=1/2(length \times width^2)$, where length is greatest longitudinal diameter and width is greatest transverse diameter. For fLuc+624 mel imaging, inoculated animals were imaged prior to and at the day of T-cell transfer and weekly thereafter. Tumors were resected immediately after euthanasia ~50-60 days after tumor cell inoculation. All in vivo assays were performed twice with similar results.

Bioluminescence Imaging

Tumor growth was monitored by Bioluminescent imaging (BLI) using the Xenogen IVIS imaging system. Photons emitted from fLuc-expressing cells within animals were quantified using Living Image software (Xenogen). Mice bearing 624 mel fLuc+ tumor cells were injected intraperitoneally with D-luciferin (150 mg/kg stock, 100 µL of D-luciferin/10 grams of body weight) in PBS and imaged under isoflurane anesthesia after 5-10 minutes. Pseudocolor images representing light intensity (blue, least intense; red, most intense) were generated using Living Image. BLI findings were confirmed at necropsy.

The results of the experiments are now described.

Naturally-occurring CD137 Expression by TILs and TALs of Ovarian Cancer

Figure 1B:
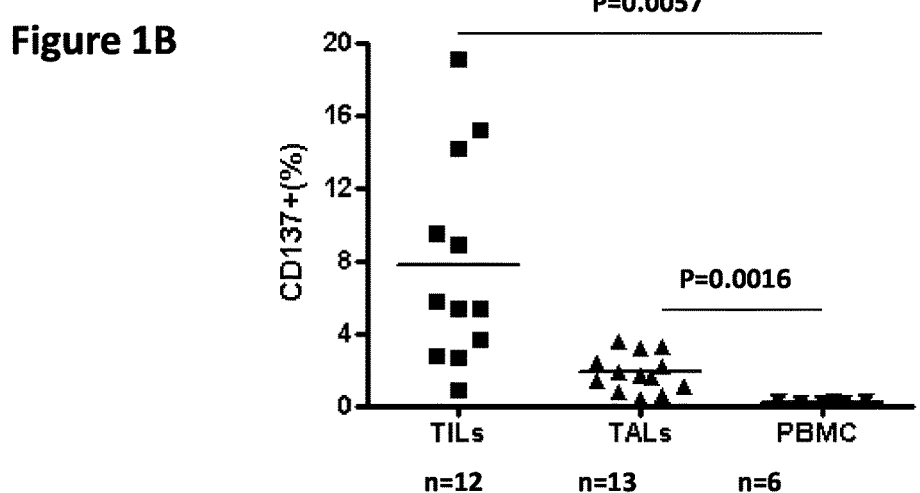
Figure 1C:
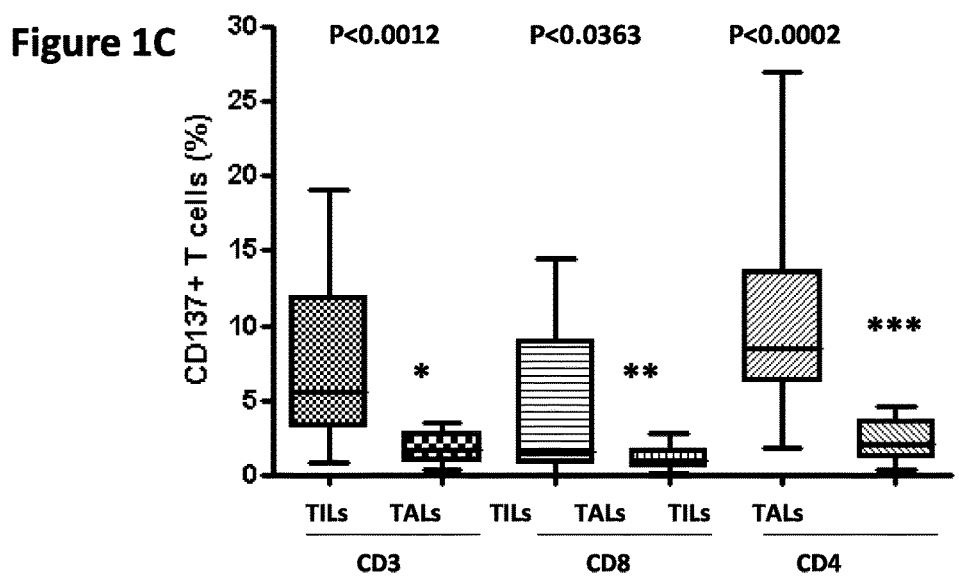

To evaluate CD137 expression T-cells from human cancer, baseline CD137 surface expression was evaluated by flow cytometry on T-cells derived directly from either enzyme-digested solid tumor (TILs), ascites (TALs) or peripheral blood from patients with ovarian cancer. CD137 expression level was significantly higher on TILs than on CD3+ T-cells from blood (0.2%±0.054, n=6, p<0.0057; FIG. 1A, B). TILs expressed CD137 at variable levels among samples (range of 0.9%-20%, mean=7.8%±5.7; n=12; FIG. 1B). The frequency of $CD137^{pos}$ TALs in ascites (1.82%±1.04, n=13) was also significantly higher than in blood (p<0.0016), but lower than in solid tumor (p<0.0012). Thus, a hierarchy exists in CD137 expression, with highest frequencies detected in intratumoral T-cells, followed by T-cells in loose association with tumor and, lastly, by blood T-cells not directly interacting with tumor cells. CD137 was expressed by both CD4+ and CD8+ T-cell subsets from solid or ascites tumor, with greater frequencies detected in TILs (FIG. 1C). There was no difference in the frequency of $CD137^{pos}$ cells between the CD4+ or CD8+ T-cell subsets in either TIL or TAL (p>0.05; FIG. 1C). Thus, patients with ovarian cancer naturally harbor T-cells with an activated $CD137^{pos}$ phenotype, preferentially in tumor sites.

Increased CD137 Expression by Fresh TILs and TALs after Overnight Incubation

Figure 2A:
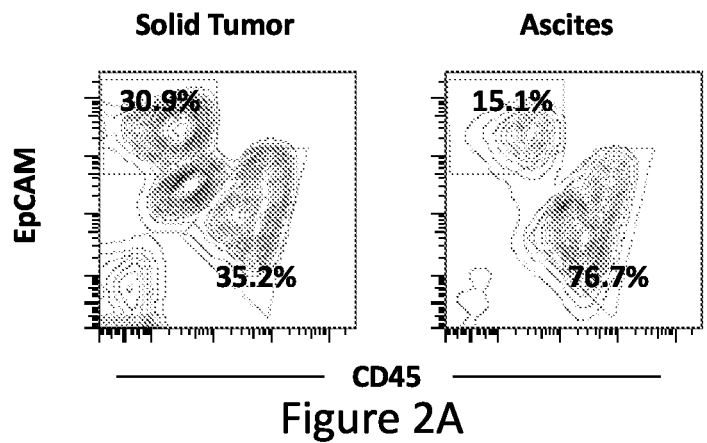
Figure 2B:
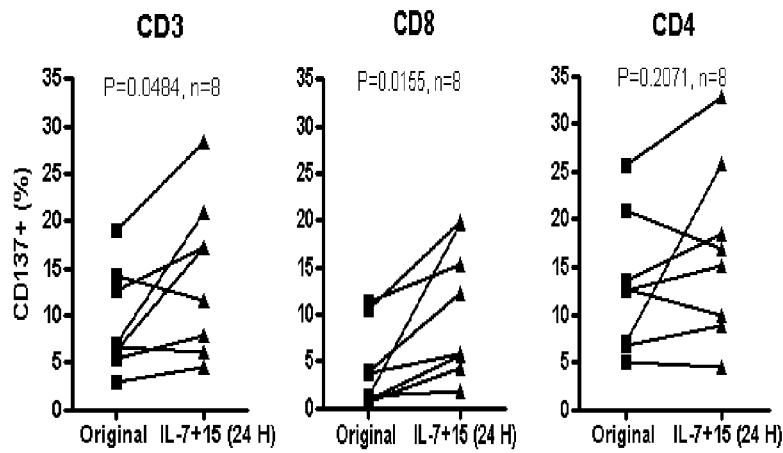
Figure 2C:
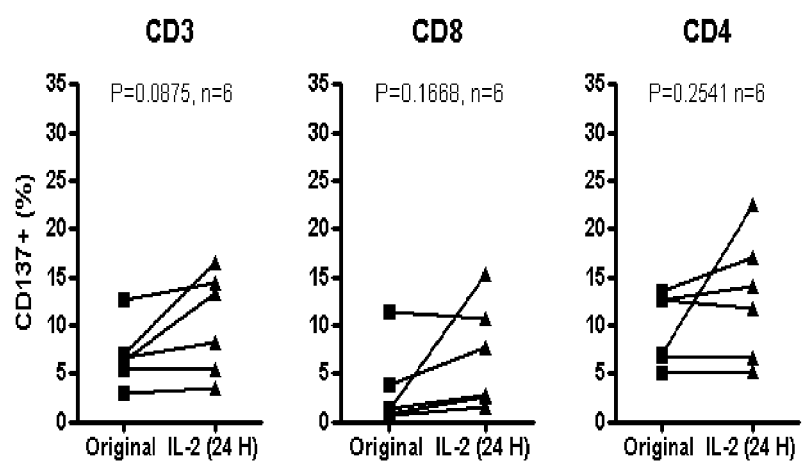

T-cell clones stimulated in vitro with cognate peptide in the presence of IL-7 and IL-15 cytokines upregulate CD137 expression within 5 hours, with peak expression after 24 hours which returns to baseline levels after 72 hours (Wolfl et al., 2007, Blood, 110: 201-10). To stimulate the broad and undefined repertoire of tumor-reactive cells in TIL or TAL, autologous tumor cell targets are required. Single cell suspensions achieved by enzyme-digestion of fresh solid human ovarian cancer, or cells directly from ascites, are comprised of both CD3+ TILs or TALs, respectively, and EpCAM+ cancer cells (FIG. 2A). The latter represent a rich autologous cell source for tumor antigen presentation and stimulation of T-cells in culture. To determine whether incubation of TILs and autologous tumor cells in the presence of T-cell growth factors results in increased CD137 expression by TILs, fresh enzyme-digested tumors were incubated in the presence of recombinant human IL-7 and IL-15 (50 ng/ml each) or IL-2 cytokine (50 IU/ml) and CD3+ TILs monitored for surface CD137 expression. The 24 hour time point was selected for analysis based upon our results showing peak CD137 expression achieved within 24-48 hours of culture, with a rapid decline after 72 hours in both cytokine conditions. In the IL-7/IL-15 condition, a significant increase in $CD137^{pos}$ CD3+ TIL frequency was observed after overnight incubation (p=0.048; FIG. 2B), with increased levels in six of eight samples tested. Notably, the $CD137^{pos}$ CD8+ TIL fraction of was significantly increased (p=0.016) in all samples. $CD137^{pos}$ CD4+ TIL frequency did not significantly increase (p=0.207), and culture of enzyme-digested tumor in media without cytokines had no significant impact on CD137 expression by CD3+ (p=0.56), CD4+ (p=0.50) or CD8+ TILs (p=0.09, n=7). Further, incubation of enzyme-digested tumors in IL-2, a T-cell growth factor commonly utilized in TIL expansion, also had no significant impact on CD137 expression by either CD3+ (p=0.09), CD4+ (p=0.25) or CD8+ TILs (p=0.17, n=6; FIG. 2C).

Similar to TILs, CD3+ TALs from fresh ascites displayed increased CD137 when incubated under IL-7/IL-15 conditions (p=0.019); 9/12 samples showed increases of ~1.5 to 10-fold (FIG. 2D). Both CD8+ and CD4+ TALs trended towards having enhanced CD137 fractions, but only the CD4+ TAL subset reached a level of significance (p=0.028). Incubation in IL-2 significantly increased the $CD137^{pos}$ CD3+ TAL fraction, but was not directly attributable to either CD4+ or CD8+ subset (FIG. 2E). $CD137^{pos}$ frequency was not increased when peripheral blood T-cells were cultured under identical conditions (FIG. 2F). CD137 upregulation was HLA-dependent since CD137 expression was diminished when enzyme-digested tumor was cultured overnight in IL-7/IL-15 cytokines in the presence of anti-HLA-ABC blocking antibodies (FIG. 2G). Thus, CD137 expression on T-cells from enzyme-digested tumors is up-regulated in an activation-induced, MHC-dependent manner ex vivo in the presence of homeostatic cytokines, IL-7 and IL-15.

CD137-expressing T-Cells from Primary Tumor Possess Autologous Tumor Reactivity

Figure 3A:
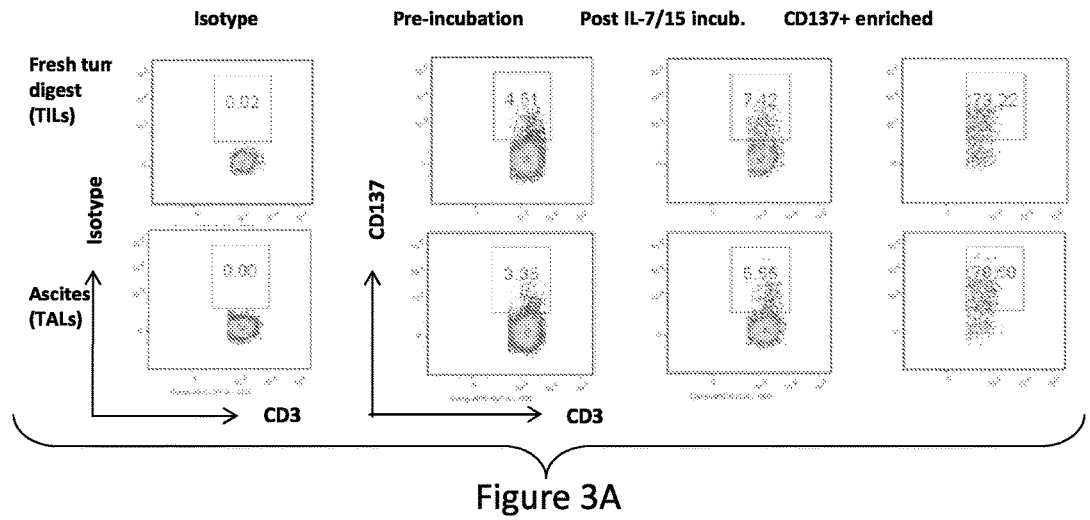
FIGS. 3A-3C, depicts the results of experiments showing CD137 enrichment from ovarian cancer TILs or TALs.
Figure 3B:
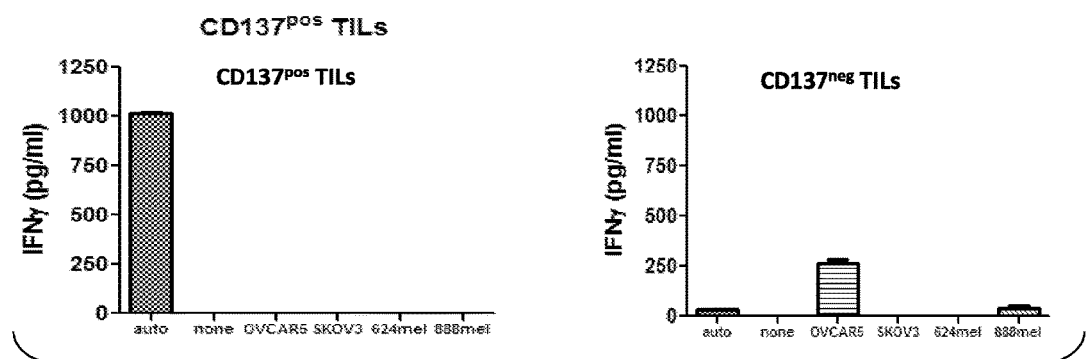
Figure 3C:
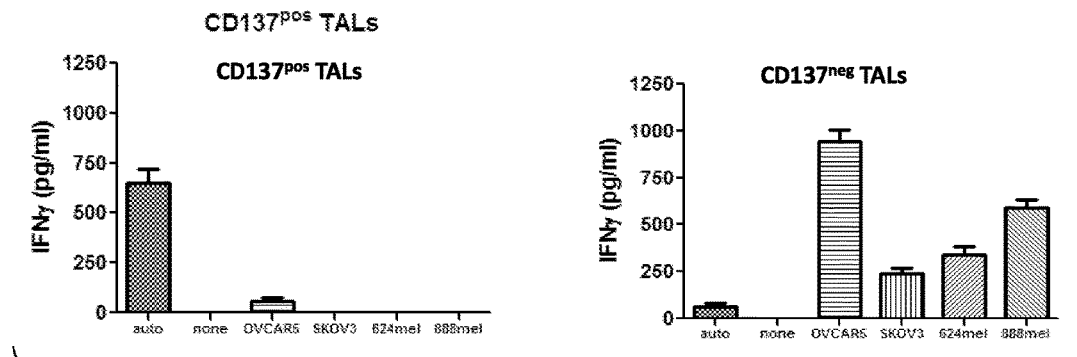

To assess whether $CD137^{pos}$ T-cells from fresh tumor are tumor-reactive, enzyme-digested tumor or ascites were cultured overnight in IL-7/IL-15 cytokines, and $CD137^{pos}$ T-cells enriched by positive magnetic bead separation. After column purification, >70% of T-cells were $CD137^{pos}$. CD137-enrichment was achievable from enzyme-digested tumors and ascites samples (representative data; FIG. 3A). $CD137^{pos}$ and $CD137^{neg}$ fractions were cultured for 8-10 days in media containing 600 IU/ml IL-2 and then tested for reactivity against autologous tumor cells in standard overnight co-culture assays. $CD137^{pos}$ TILs or TALs secreted IFN-γ cytokine in response to autologous tumor cell stimulation; $CD137^{neg}$ counterparts did not respond (FIG. 3B, 3C). CD137 upregulation was antigen-driven since $CD137^{pos}$ and $CD137^{neg}$ TILs and TALs did not spontaneously secrete IFN-γ, and non-specific responses to HLA-mismatched tumors were restricted to $CD137^{neg}$ fractions.

Figure 6A:
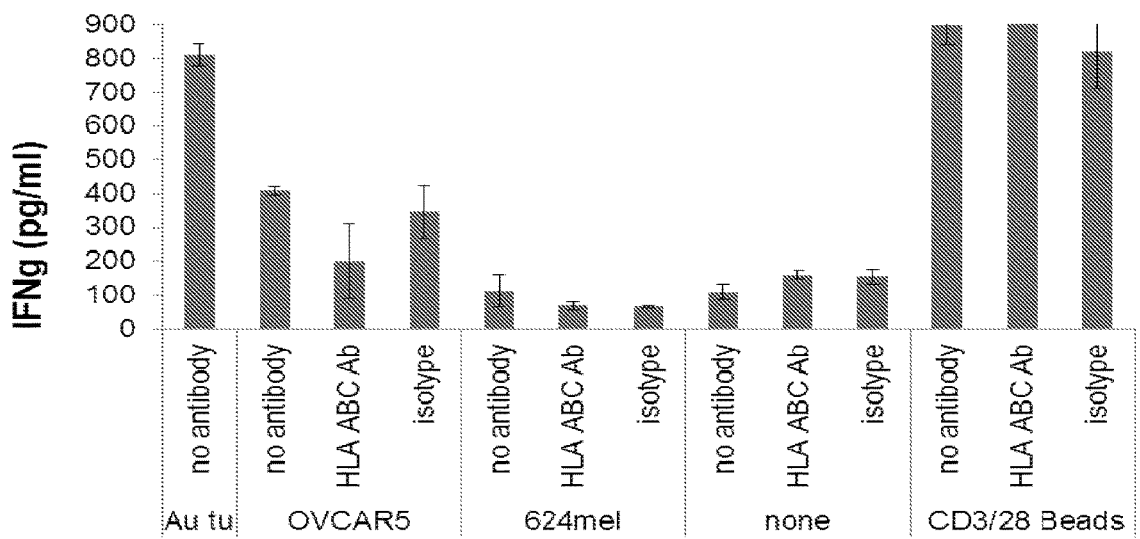
FIGS. 6A-6B, depicts the results of experiments demonstrating that ovarian cancer contains tumor specific reactive T cells.
Figure 6B:
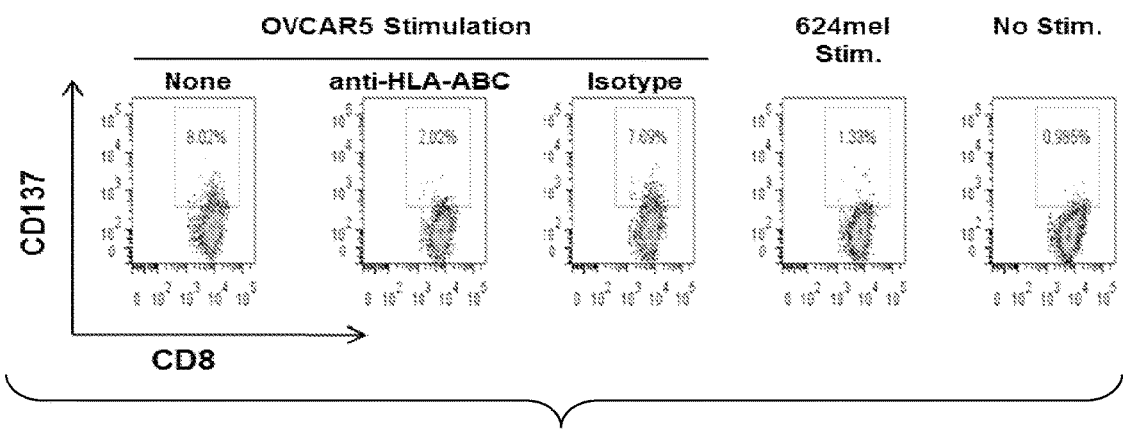

To confirm that reactivity in $CD137^{pos}$ T-cells from ovarian cancer is peptide/HLA-dependent, an ovarian TAL line (1555) from an HLA-A2+ donor was identified which recognized autologous tumor, as well as a shared antigen expressed by the HLA-A2+ tumor cell line, OVCAR5. In overnight co-culture, 1555TALs secreted IFN-γ in response to autologous tumor or OVCAR5 stimulation, but not to non-HLA matched lines (FIG. 6A). Reactivity was inhibited by addition of anti-HLA-ABC blocking antibodies to the OVCAR5 co-culture, implicating a class-I restricted CD8+ TAL response. Prior to co-culture, ~1% of CD8+ 1555TALs expressed CD137. Following culture with OVCAR5, ~8% of CD8+ TALs were $CD137^{pos}$ (FIG. 6B). Consistent with inhibited cytokine responses, antibody blockade of MHC class I decreased the fraction of $CD137^{pos}$ TALs by ~75%. Thus, short-term culture of TILs or TALs from primary tumor in the presence of autologous or HLA-matched tumor cells results in activation-induced CD137 upregulation, which can serve as a biomarker for the identification and enrichment of T-cells with HLA-restricted tumor reactivity.

Tumor Antigen-Specific TILs Upregulate CD137 after Stimulation with Tumor

Due to the paucity of tumor antigen-specific TILs of known specificity in ovarian cancer, four established HLA-A2+ melanoma TIL lines, three with defined MART-1:26-35 peptide specificity, were used as an in vitro model system to test whether CD137 identifies the tumor antigen-specific T-cell population in TIL. Prior to stimulation, MART-1 specific T-cells were detectable by tetramer staining at various frequencies in TILs #1, #2 and #3 (FIG. 4A) and CD137 expression was low (average of 0.9±0.6%) on tetramer-positive and negative TIL populations. After overnight co-culture with the HLA-A2+ MART-1-expressing melanoma line 624 mel, but not HLA-A2-negative 938 mel, ~90% of MART-1 tetramer-positive TILs expressed surface CD137. TIL#2 and TIL#3 also upregulated CD137 expression in the tetramer-negative population suggesting shared tumor antigen recognition. TIL#2 also possessed a subset of tetramer-negative TILs with cross-reactivity against 938 mel in repeated assays. TIL#4, which lacks detectable MART-1-specific T-cells but possesses shared HLA-A2-restricted tumor antigen reactivity, upregulated CD137 in the tetramer-negative population upon stimulation with 624 mel, but not 938 mel.

Figure 4A:
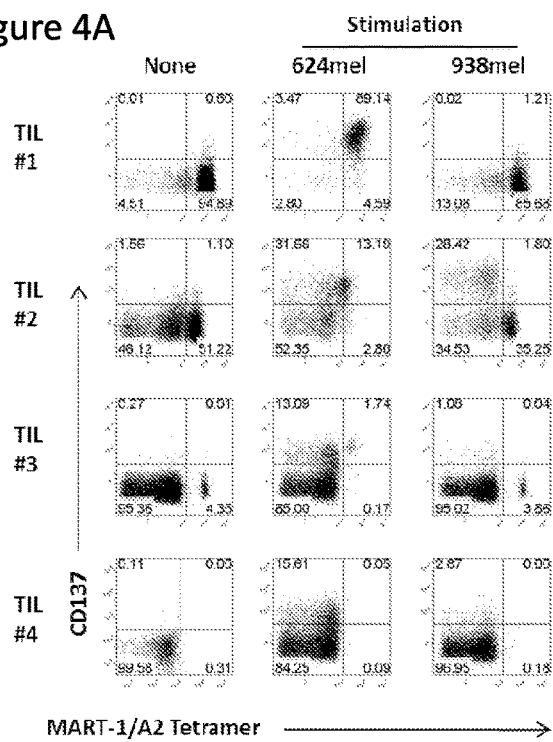
FIGS. 4A-4E, depicts the results of experiments demonstrating enhanced potency of CD137-enriched melanoma-reactive TILs.
Figure 4C:
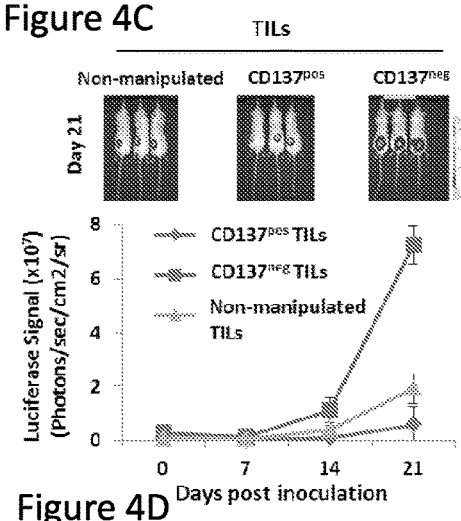
Figure 4D:
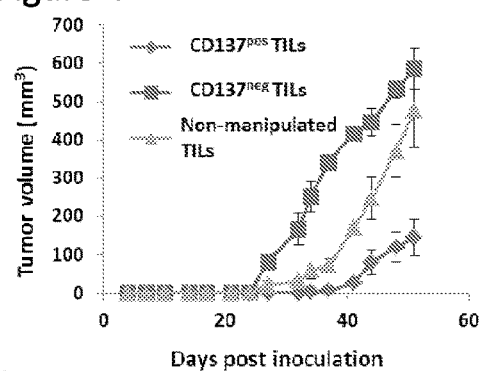
Figure 4B:
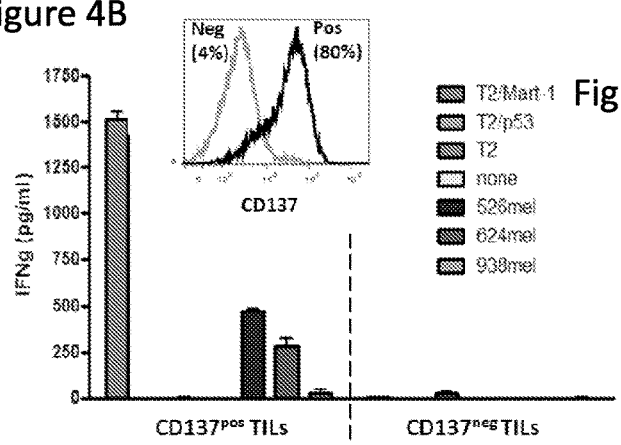

To assess whether $CD137^{pos}$ TILs in melanoma possess antigen-specific anti-tumor reactivity, TIL#2 was stimulated with 624 mel cells overnight and subsequently enriched for $CD137^{pos}$ and negative fractions (FIG. 4B). Nearly all MART-1 tetramer-positive cells were contained within the $CD137^{pos}$ T-cell fraction (FIG. 4A). One week later, TIL fractions were stimulated with peptide-pulsed T2 APCs or HLA-matched melanoma lines, 526 mel and 624 mel, or mismatched line, 938 mel. Consistent with CD137 expression and tetramer staining results, $CD137^{pos}$ TILs secreted IFN-γ when stimulated with MART-1 peptide-pulsed T2 cells, or 526 mel and 624 mel lines, but not when stimulated with irrelevant peptide-pulsed T2 cells or with HLA-A2-negative 938 mel cells (FIG. 4B). $CD137^{neg}$ TILs did not respond to MART-1 peptide or tumor stimulation. Thus, the tumor-stimulated $CD137^{pos}$ T-cell fraction from melanoma TIL lines identifies a subset of T-cells with known and unknown tumor antigen-specificity.

$CD137^{pos}$, but not $CD137^{neg}$, TILs Inhibit Tumor Growth In Vivo

Figure 4E:
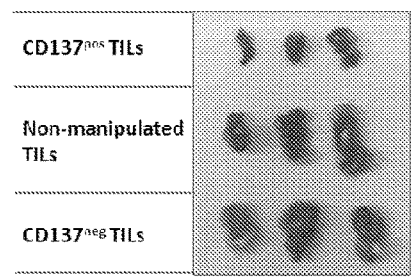

Next, the capacity of CD137-enriched TILs to inhibit tumor outgrowth in vivo was evaluated. After overnight co-culture of TIL#2 and 624 mel cells, $CD137^{pos}$ and $CD137^{neg}$ fractions were isolated and rested in media for 10 days. $CD137^{pos}$, $CD137^{neg}$ or non-manipulated TILs were subcutaneously co-injected with an equal number of firefly luciferase-transfected 624 mel cells in the hindquarters of immunodeficient NOD/SCID/IL-2Rγc$^{null}$ (NSG) mice in a modified Winn assay. Tumor outgrowth was measured by photon emission imaging and caliper measurement. Three weeks post-inoculation, a strong delay in tumor outgrowth was observed in mice treated with $CD137^{pos}$ TIL compared to $CD137^{neg}$ and non-manipulated TIL groups as measured by bioluminescence signal detection (FIG. 4C, p=0.00037, $CD137^{pos}$ versus $CD137^{neg}$; p=0.038, $CD137^{pos}$ versus non-manipulated TILs). Four weeks after inoculation, measurable tumor emerged in mice that received $CD137^{neg}$ or non-manipulated TILs; no palpable tumors were detected in mice receiving $CD137^{pos}$ TILs until 42 days after inoculation. At the end of study, non-manipulated TILs mediated a modest inhibition in tumor outgrowth compared to $CD137^{neg}$ TILs, though not statistically significant (p=0.375, FIG. 4D). In contrast, a significant reduction in measurable tumor outgrowth was observed in $CD137^{pos}$ TIL-treated mice relative to $CD137^{neg}$ (p=0.016) and non-manipulated TIL groups (p=0.0354). These results were confirmed by direct morphological sizing of tumors resected from euthanized mice (FIG. 4E).

Figure 7A:
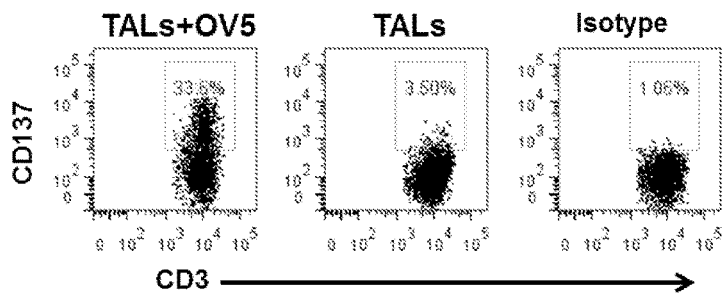
Figure 7B:
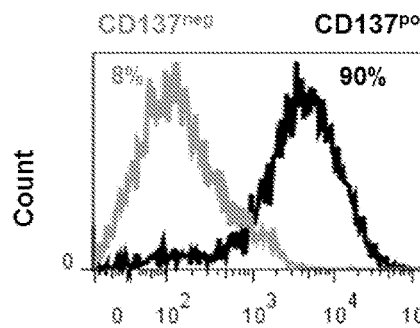
Figure 7C:
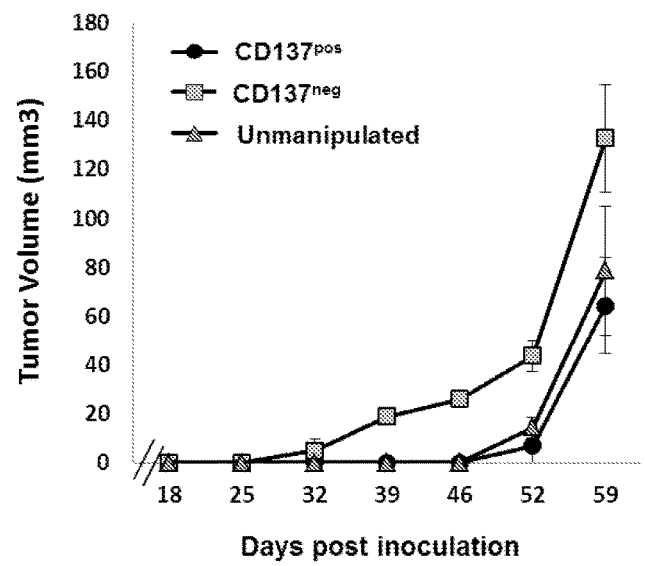
Figure 7D:
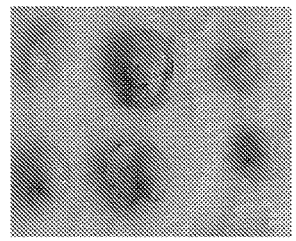
Figure 7D:
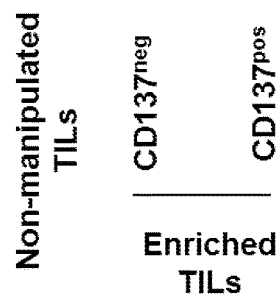

Adoptive TIL therapy has been explored extensively for melanoma, but less so for ovarian cancer where isolation of tumor-reactive T-cells from tumors is more challenging (Freedman et al., 1994, J Immunol Methods, 167:145-60; Ioannides et al., 1991, J Immunol, 146: 1700-7; Fujita et al., 1995, Clin Cancer Res, 1:501-7; Aoki et al., 1991, Cancer Res, 51:1934-9). To determine whether CD137 selection of T-cells derived from ovarian cancer yields a cell population with anti-tumor potency in vivo, tumor-reactive HLA-A2-restricted TALs were stimulated with OVCAR5 cells under IL-7/15 conditions and enriched for CD137 by positive magnetic selection for use in a modified Winn assay. After tumor stimulation, 34% of TALs expressed CD137 (FIG. 7A) and were subsequently enriched to 90% $CD137^{pos}$ (FIG. 7B). After 10 days, non-manipulated, $CD137^{pos}$ or $CD137^{neg}$ TALs were subcutaneously co-inoculated with OVCAR5 tumor cells into the hind quarters of NSG mice and monitored for tumor outgrowth by caliper-based measurement. Measurable tumors were detectable in mice receiving $CD137^{neg}$ TALs 32 days after inoculation, while detectable tumor growth was delayed until day 52 in mice receiving either non-manipulated or $CD137^{pos}$ TALs (FIG. 7C). Two months after inoculation, tumor outgrowth was significantly inhibited in the $CD137^{pos}$ TAL group compared to the $CD137^{neg}$ group (p=0.035), with a similar but non-significant trend for non-manipulated TILs (p=0.076). Increased inhibition of tumor outgrowth was observed in mice receiving $CD137^{pos}$ TALs compared to non-manipulated TALs, but not to the level of statistical significance (p=0.498). Caliper-based sizing results were confirmed by direct morphological sizing of lesions harvested from euthanized mice (FIG. 7D).

CD137, not PD-1, Accurately Identifies Tumor-Reactive TILs

Figure 5A:
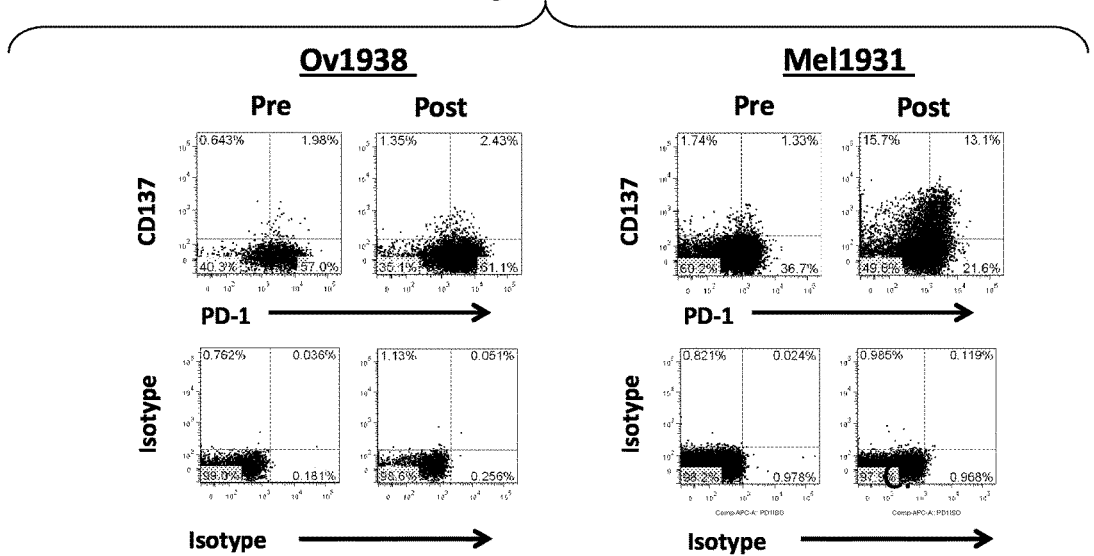
FIGS. 5A-5C, depicts the results of experiments demonstrating that CD137 expression is more restricted than PD-1 on fresh and tumor-stimulated TILs.
Figure 5B:
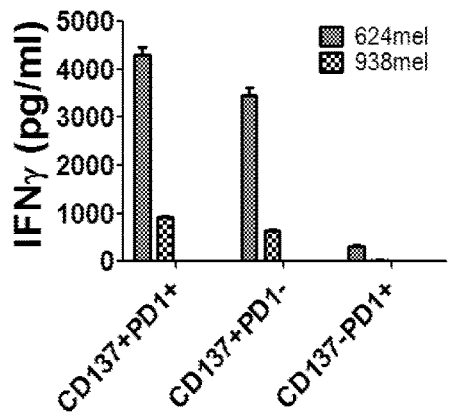
Figure 5C:
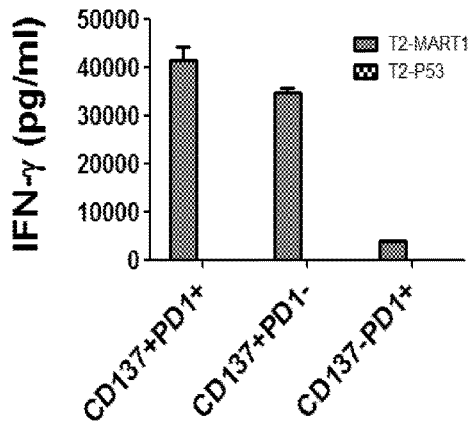

Programmed cell death-1 (PD-1, PDCD1, CD279) receptor is a negative immunoregulatory molecule expressed by activated T-cells that plays an important role in the immunobiology of cancer (Topalian et al., 2012, N Engl J Med, 366: 2443-54; Brahmer et al., 2012, N Engl J Med, 366: 2455-65). PD-1 can be a useful biomarker for enriching tumor-specific T-cells from fresh melanomas where there is an observed higher tumor-specific IFN-γ production by PD-1+CD8+ TILs compared with PD-1$^{neg}$ T-cells (Inozume et al., 2010, J Immunother, 33: 956-64). TILs from fresh enzyme-digested ovarian tumors were measured for their relative expression of CD137 and PD-1 either fresh or after overnight incubation in IL-7/15. Prior to incubation, up to 60% of TILs expressed surface PD-1 (mean of 46%±13), while only 3.6%±1.7 expressed CD137 (n=3; representative data shown in FIG. 5A). After overnight culture in IL-7/15, the percentage of $CD137^{pos}$ TILs increased to 4.6%±1.2 (Table 1), while 50%±13 expressed PD-1. Under both conditions, only a small portion of PD-1+ TILs co-expressed CD137; the majority was $CD137^{neg}$. Small frequencies of $CD137^{pos}$ cells were also detected in the PD-1$^{int/neg}$ fraction. Similar phenotypic results were observed using HLA-A2-restricted, tumor-reactive melanoma TIL lines that were stimulated with 624 mel cells. Functional assessment of FACS-sorted $CD137^{pos}$PD-1+, $CD137^{pos}$PD-1$^{neg}$, and $CD137^{neg}$PD-1+ TIL subsets revealed a dichotomy in tumor antigen-specific reactivity. $CD137^{pos}$PD-1+ and $CD137^{pos}$PD-1$^{neg}$ TILs responded specifically to stimulation with either the HLA-matched, MART-1+ 624 mel or MART-1 peptide pulsed T2 cells with modestly greater activity observed from $CD137^{pos}$PD-1+ TILs; $CD137^{neg}$PD-1+ TILs did not respond to either stimulus (FIGS. 5B,C). This data, coupled with the reproducible observation that $CD137^{pos}$ TIL (but not $CD137^{neg}$+/−PD-1) enrichment leads to comprehensive isolation of tumor-reactive TILs in melanoma and ovarian cancer (FIGS. 3B, 4B), indicates that CD137 more accurately identifies the subset of TILs and TALs with antitumor activity than PD-1.

TABLE 1

Relative expression of CD137 and PD-1 on tumor-activated TILs

| Subset | Ovarian TILs | | | | | Melanoma TILs | |
|---|---|---|---|---|---|---|---|
| | 1938 | 1922 | 1913 | Mean | SEM | 1913 | 1979 |
| CD137+ | 3.78 | 6.89 | 3.17 | 4.6 | 1.2 | 28.8 | 20.67 |
| PD-1+ | 63.53 | 64.28 | 23.92 | 50.6 | 13.3 | 34.7 | 22.07 |
| CD137+ PD-1+ | 2.43 | 5.18 | 1.22 | 2.9 | 1.2 | 13.1 | 6.57 |
| CD137+ PD-1− | 1.35 | 1.71 | 1.95 | 1.7 | 0.2 | 15.7 | 14.1 |
| CD137− PD-1+ | 61.1 | 59.1 | 22.7 | 47.6 | 12.5 | 21.6 | 15.5 |
| CD137− PD-1− | 35.1 | 34 | 74.1 | 47.7 | 13.2 | 49.6 | 63.8 |

Enzyme-digested ovarian cancer specimens (1938, 1922, 1913) were cultured overnight in the presence of Interleukins-7 and -15, harvested and stained and measured for viable CD3+ TILs expressing CD137 and programmed cell death-1 (PD-1) receptor by flow cytometry. For melanoma TIL lines (1913, 1979), HLA-A2 restricted TILs were co-cultured with the HLA-A2+ 624 melanoma cell line, or HLA-A2-line, 938 (not shown). Quadrant gates were established based upon isotype Ig staining for each individual TIL tested. Values represent the percentage of viable (7-AAD-) CD3+ TILs expressing the indicated surface molecule.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of culturing tumor-reactive T cells, the method comprising isolating and culturing a population of CD137+ cells from a sample of solid tumor tissue, wherein the population of CD137+ cells comprises the tumor-reactive T cells, and further wherein the population of CD137+ cells is cultured in the presence of at least one of IL-7 and IL-15.

2. The method of claim 1, wherein the population of CD137+ cells comprises one or more of tumor-infiltrating lymphocytes (TIL), cytotoxic T lymphocytes (CTL), natural killer (NK) cells, and lymphokine-activated killer (LAK) cells.

3. The method of claim 1, wherein the population of CD137+ cells comprises PD-1+ cells.

4. The method of claim 1, wherein the solid tumor tissue comprises cancer cells.

5. The method of claim 1, wherein the solid tumor tissue comprises tumor antigens that have been exposed to the tumor-reactive T cells.

6. A method of culturing tumor-reactive T cells, the method comprising enzymatically digesting a solid tumor tissue prior to isolating and culturing a population of CD137+ cells from a sample of the solid tumor tissue, wherein the population of CD137+ cells comprises the tumor-reactive T cells.

7. A method of culturing tumor-reactive T cells, the method comprising:
(a) isolating and culturing for about 7 days a population of CD137+ cells from a sample of solid tumor tissue, wherein the population of CD137+ cells comprises the tumor-reactive T cells; and
(b) administering the population of CD137+ cells to a subject in need thereof.

8. The method of claim 7 further comprising expanding the population of CD137+ cells prior to administering to the subject.

9. The method of claim 1 further comprising culturing the population of CD137+ cells in a presence of an immune cell stimulating ligand.

10. The method of claim 9, wherein the immune cell stimulating ligand is at least one selected from the group consisting of an anti-CD3 antibody and an anti-CD28 antibody.

11. A method of culturing tumor-reactive T cells, the method comprising isolating and culturing a population of CD137+ cells from a sample of solid tumor tissue, wherein the population of CD137+ cells comprises the tumor-reactive T cells, and further wherein the population of CD137+ cells is co-cultured with a HLA-matched tumor cell line.

12. The method of claim 11, wherein the population of CD137+ cells produce IFN-γ after co-culturing with the HLA-matched tumor cell line.

13. A method of culturing tumor-reactive T cells, the method comprising isolating and culturing CD137+ cells from a sample of solid tumor tissue in a closed-chamber, wherein the population of CD137+ cells comprises the tumor-reactive T cells, and further wherein the population of CD137+ cells is cultured in the presence of at least one of IL-7 and IL-15.

* * * * *